United States Patent
Ditrich et al.

Patent Number: 5,217,523
Date of Patent: Jun. 8, 1993

[54] PYRAZOLE-3-CARBOXAMIDES, HERBICIDAL COMPOSITIONS AND USE

[75] Inventors: Klaus Ditrich, Bad Durkheim; Gerhard Hamprecht, Weinheim; Peter Plath, Frankenthal; Bruno Wuerzer, Ottenstadt; Karl-Otto Westphalen, Speyer, all of Fed. Rep. of Germany

[73] Assignee: BASF Aktiengesellschaft, Ludwigshafen, Fed. Rep. of Germany

[21] Appl. No.: 877,366

[22] Filed: May 4, 1992

Related U.S. Application Data

[63] Continuation of Ser. No. 580,471, Sep. 11, 1990, abandoned.

[30] Foreign Application Priority Data

Sep. 23, 1989 [DE] Fed. Rep. of Germany ....... 3931786

[51] Int. Cl.$^5$ .................... A01N 43/56; C07D 231/14
[52] U.S. Cl. ........................ 504/280; 504/193; 504/196; 504/197; 504/282; 504/253; 504/270; 504/249; 504/250; 504/266; 504/191; 504/248; 504/269; 548/374.1; 504/270; 504/271; 504/277; 504/239
[58] Field of Search ............ 548/374.1; 71/92

[56] References Cited

U.S. PATENT DOCUMENTS 4,892,956 1/1990 Rizzo et al. ............ 548/356
5,053,517 10/1991 Takigawa et al. ............ 548/377

FOREIGN PATENT DOCUMENTS 0286279 10/1988
0350176 1/1990 European Pat. Off.

OTHER PUBLICATIONS

Bastide et al , Chem Abstracts, vol. 75 (1971) No. 35874p.
Matsui et al, Chem Abstracts, vol. 77 (1972) Mo. 34554p.
Gutierrez, Chem. Abstracts, vol. 96 (1982) No. 142849a.

Primary Examiner—Robert W. Ramsuer
Attorney, Agent, or Firm—Keil & Weinkauf

[57] ABSTRACT

Pyrazole-3-carboxamides of the general formula I

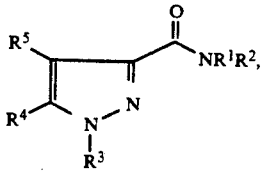

where the substituents have the following meaning:
$R^1$ hydrogen;
  substituted or unsubstituted $C_3$–$C_8$-cycloalkyl or $C_1C_6$-alkyl;
$R^2$ hydroxy; amino; $C_1$–$C_4$-aklylamino; di-$C_1$–$C_4$-alkylamino, aminocarbonyl-$C_1$–$C_6$-alkyl; substituted or unsubstituted $C_1$–$C_4$-alkoxy, $C_3$–$C_6$-alkenyl, $C_3$–$C_6$-alkynyl, phenyl or naphthyl,
  a substituted or unsubstituted 5- to 6-membered heterocyclic ring;
  one of the groups mentioned for $R^1$ or
  $R^1$ and $R^2$ together denote a 4- to 7-membered chain which may contain, in addition to methylene groups one of the following groups as ring member: oxygen, sulfur N-methyl or carbonyl;
$R^3$ a substituted or unsubstituted 5- to 6-membered heterocyclic ring.
  substituted or unsubstituted $C_3$–$C_6$-alkenyl, $C_3$–$C_6$alkynyl, 5,6,7,8-tetrahydronaphthyl or phenyl or
  one of the groups mentioned for $R^1$;
$R^4$ nitro; cyano; carboxyl; halogen; substituted or unsubstituted $C_1$–$C_4$-alkoxy or $C_1$–$C_4$-alkylthio, or one of the groups mentioned for $R^3$;
$R^5$ 4,5-dihydrooxazol-2-yl or a group COYR$^6$;
Y hydrogen;
$R^6$ $C_3$–$C_8$-cycloalkyl, substituted or unsubstituted $C_1$–$C_6$-alkyl, $C_3$–$C_6$-alkenyl, $C_3$–$C_6$-alkynyl, $C_5$–$C_7$-cycloalkenyl or phenyl,
  a substituted or unsubstituted 5- or 6-membered heterocyclic ring; phthalimido; tetrahydrophthalimido; succinimido; maleiimido; benzotriazolyl or
  a group —N=CR$^7$R$^8$, where
$R^7$ is hydrogen or $C_1$–$C_6$-alkyl and
$R^8$ is $C_3$–$C_6$-cycloalkyl, phenyl, furyl or a radical $R^7$ or
$R^7$, $R^8$ together denote a 4- to 7-membered alkylene chain,
and their agriculturally useful salts, Y not denoting oxygen and $R^1$ not denoting hydrogen when $R^3$ is hydrogen and $R^4$ is nitro, trifluoromethyl, halogen or $C_1$–$C_4$-alkoxy and —YR$^6$ not denoting ethoxy when $R^1$ is hydrogen, $R^4$ is methyl and $R^2$ is phenyl or substituted phenyl.

6 Claims, No Drawings

PYRAZOLE-3-CARBOXAMIDES, HERBICIDAL COMPOSITIONS AND USE

This application is a continuation of application Ser. No. 07/580,471, filed on Sep. 11, 1990, now abandoned.

The present invention relates to pyrazole-3-carboxamides of the general formula I

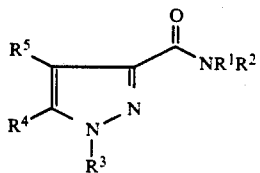

where
R$^1$ is hydrogen;
C$_3$–C$_8$-cycloalkyl which may carry from one to three of the following radicals: halogen, C$_1$–C$_4$-alkyl, C$_1$–C$_4$-haloalkyl, C$_1$–C$_4$-alkoxy and/or C$_1$–C$_4$-haloalkoxy;
C$_1$–C$_6$-alkyl which may carry from one to three of the following radicals: hydroxyl, halogen, C$_1$–C$_4$-alkoxy, C$_1$–C$_4$-haloalkoxy, C$_1$–C$_4$-alkylthio, C$_1$–C$_4$-haloalkylthio, hydroxycarbonyl, C$_1$–C$_4$-alkoxycarbonyl, C$_1$–C$_4$-alkylamino, di-C$_1$–C$_4$-alkylamino and/or C$_3$–C$_6$-cycloalkylamino and/or a radical

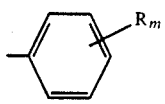

where
R is cyano; nitro; halogen; C$_1$–C$_4$-alkyl; C$_1$–C$_4$-haloalkyl; C$_1$–C$_4$-alkoxy; C$_1$–C$_4$-haloalkoxy; C$_1$–C$_4$-alkylthio; C$_1$–C$_4$-haloalkylthio and/or C$_1$–C$_4$-alkoxycarbonyl, and
m is 0, 1, 2 or 3, it being possible for the radicals R to be different from one another when m is 2 or 3;
R$^2$ is hydroxyl; amino; C$_1$–C$_4$-alkylamino; di-C$_1$–C$_4$-alkylamino; aminocarbonyl-C$_1$–C$_6$-alkyl; C$_1$–C$_4$-alkoxy which may carry a radical

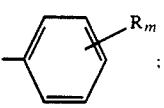

C$_3$–C$_6$-alkenyl, C$_3$–C$_6$-alkynyl, phenyl or naphthyl, it being possible for these groups to carry from one to three of the radicals mentioned in the case of R;
a 5- to 6-membered saturated or unsaturated heterocyclic ring containing one or two heteroatoms selected from the group comprising nitrogen, oxygen and sulfur, it being possible for this ring to carry one or two of the following radicals: halogen, C$_1$–C$_4$-alkyl, C$_1$–C$_4$-haloalkyl, C$_1$–C$_4$-alkoxy, C$_1$–C$_4$-haloalkoxy and/or C$_1$–C$_4$-alkylthio;
one of the groups mentioned in the case of R$^1$ or
R$^1$ and R$^2$ together are a 4- to 7-membered chain which may contain one of the following groups as a ring member in addition to methylene groups: oxygen, sulfur, N-methyl or carbonyl;
R$^3$ is a 5- to 6-membered saturated or unsaturated heterocyclic ring containing one or two heteroatoms selected from the group comprising oxygen, sulfur and nitrogen, it being possible for this ring to carry one or two of the following radicals: halogen, C$_1$–C$_4$-alkyl, C$_1$–C$_4$-haloalkyl, C$_1$–C$_4$-alkoxy, C$_1$–C$_4$-haloalkoxy and/or C$_1$–C$_4$-alkylthio;
C$_3$–C$_6$-alkenyl, C$_3$–C$_6$-alkynyl-, 5,6,7,8-tetrahydronaphthyl or phenyl, it being possible for these groups to carry from one to three of the radicals mentioned in the case of R, or
is one of the groups mentioned in the case of R$^1$;
R$^4$ is nitro; cyano; carboxyl; halogen;
C$_1$–C$_4$-alkoxy or C$_1$–C$_4$-alkylthio, it being possible for these groups to carry from one to nine halogen atoms, or is one of the groups mentioned in the case of R$^3$;
R$^5$ is 4,5-dihydrooxazol-2-yl or a COYR$^6$ group;
Y is oxygen or sulfur;
R$^6$ is hydrogen;
C$_3$–C$_8$-cycloalkyl;
C$_1$–C$_6$-alkyl which may carry from one to five halogen atoms or hydroxyl groups and/or one of the following radicals: cyano, aminocarbonyl, carboxyl, trimethylsilyl, C$_1$–C$_4$-alkoxy, C$_1$–C$_4$-alkoxy-C$_2$–C$_4$-alkoxy, C$_1$–C$_4$-alkylthio, C$_1$–C$_4$-alkylamino, di-C$_1$–C$_4$-alkylamino, C$_1$–C$_4$-alkylsulfinyl, C$_1$–C$_4$-alkylsulfonyl, C$_1$–C$_4$-alkoxycarbonyl, C$_1$–C$_4$-alkylaminocarbonyl, di-C$_1$–C$_4$-alkylaminocarbonyl, di-C$_1$–C$_4$-alkylphosphonyl, C$_1$–C$_4$-alkyliminoxy, phenyl, thienyl, benzyloxy, benzylthio, furyl, tetrahydrofuryl, phthalimido, pyridyl and/or benzoyl, it being possible for the cyclic radicals to themselves carry from one to three of the radicals mentioned in the case of R;
C$_3$–C$_6$-alkenyl, C$_3$–C$_6$-alkynyl- or C$_5$–C$_7$-cycloalkenyl, it being possible for these groups to carry one of the following radicals hydroxyl, halogen, C$_1$–C$_4$-alkoxy or phenyl, it being possible for the phenyl radical to itself carry from one to three of the radicals mentioned in the case of R;
a 5- to 6-membered saturated or unsaturated heterocyclic ring containing one or two heteroatoms selected from the group comprising nitrogen, oxygen and sulfur;
phthalimido; tetrahydrophthalimido; succinimido; maleiimido; benzotriazolyl;
phenyl which may carry from one to three of the radicals mentioned in the case of R;
an —N=CR$^7$R$^8$ group where
R$^7$ is hydrogen or C$_1$–C$_6$-alkyl and
R$^8$ is C$_3$–C$_6$-cycloalkyl, phenyl, furyl or a radical R$^7$, or
R$^7$ and R$^8$ together form a 4- to 7-membered alkylene chain,
and agriculturally useful salts thereof, where Y is not oxygen or R$^1$ is not hydrogen if R$^3$ is hydrogen and R$^4$ is nitro, trifluoromethyl, halogen or C$_1$–C$_4$-alkoxy.

The present invention also relates to herbicides containing one or more pyrazole-3-carboximides I and/or pyrazole-3-carboximides of the general formula Ia

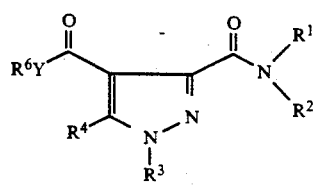

where Y is oxygen or $R^1$ is hydrogen if $R^3$ is hydrogen and $R^4$ is nitro, trifluoromethyl, halogen or $C_1$–$C_4$-alkoxy, and inert additives.

Pyrazole-3-carboximides are known from the literature for the following applications:

| Application | Literature citation |
|---|---|
| Additive for electrocoating paints | EP-A 159 117 |
| Fungicide | EP-A 206 523 |
| — | Indian. J. Chem. 13, (1975) 655 |

In addition, DE-A-33 32 633 describes pyrazole-3-carboxamides which are substituted in the 5-position of the heterocyclic ring by nitro, trifluoromethyl, halogen or $C_1$–$C_4$-alkoxy, as pharmaceuticals.

However, a herbicidal action of substances of this type was not found.

It is an object of the present invention to provide novel herbicidally active substances.

We have found that this object is achieved by the pyrazole-3-carboxamides I defined at the outset.

We have also found that the pyrazole-3-carboxamides I and the pyrazole-3-carboxamides Ia are suitable for controlling undesired plant growth.

The pyrazole-3-carboxamides I according to the invention can be prepared by various processes, for example by the following:

1. A process for the preparation of a compound I in which $R^5$ is $CO_2R'$ and $R'$ is $C_1$–$C_4$-alkyl

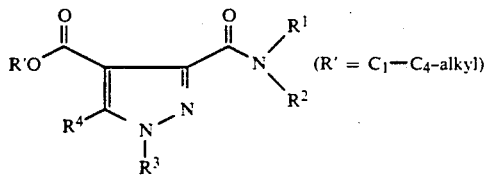

These pyrazole-3-carboxamides I are obtained by reacting a dialkyl pyrazole-3,4-dicarboxylate of the formula II in a conventional manner in an inert organic solvent with an amine of the formula III

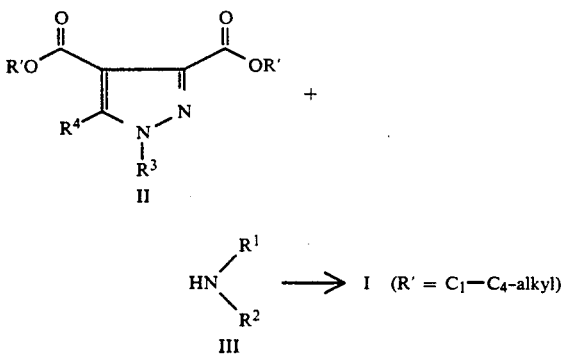

R' in the formulae II and I is $C_1$–$C_4$-alkyl, such as methyl, ethyl, propyl, 1-methylethyl, butyl, 1-methylpropyl, 2-methylpropyl or 1,1-dimethylethyl, preferably methyl, ethyl or 1-methylethyl.

The reaction is generally carried out at from 0° to 100° C., preferably from 50° to 80° C., in an inert organic solvent.

Suitable solvents are halogenated hydrocarbons, such as chlorobenzene and 1,2-dichlorobenzene, ethers, such as methyl tert-butyl ether, 1,2-dimethoxyethane, diethylene glycol dimethyl ether, tetrahydrofuran and dioxane; alcohols, such as methanol, ethanol, propanol and ethylene glycol, dipolar aprotic solvents, such as acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolin-2-one, or aromatic compounds, such as benzene, toluene and xylene. The process is particularly preferably carried out in the alcohol corresponding to the ester component.

The concentration of the starting materials in the solvent is generally from 0.1 to 5.0 mol/l, preferably from 0.2 to 2.0 mol/l.

The molar ratio between II and III is generally from 1:2.5 to 1:1, preferably from 1:1.5 to 1:1.

A particularly preferred process involves the use of a diester II and an amine III in the ratio 1:1 in the absence of solvents at from 50° to 80° C.

The pyrazoledicarboxylates II required as starting materials for this process are known from the literature or can be prepared by methods known from the literature (cf. J. Heterocyclic Chem. 25, (1988) 1293; J. Am. Chem. Soc. 73, (1951) 3684; J. Org. Chem. 31, (1966) 2491; J. Heterocyclic Chem. 22, (1985) 565; Chem. Ber. 101, (1968) 536; Chem. Ber. 101, (1968) 1059; Chem. Ber. 107, (1974) 3036).

The amines V required are either commercially available or can be prepared by conventional processes.

A particularly preferred process for the preparation of the pyrazole-3-carboxamides of the formula I comprises converting a pyrazole-3,4-dicarboxylate of the formula IIa into a monocarboxylic acid IIb using an aqueous base. The compound IIb can be converted into the desired amide via the acyl chloride intermediate using an amine of the formula III.

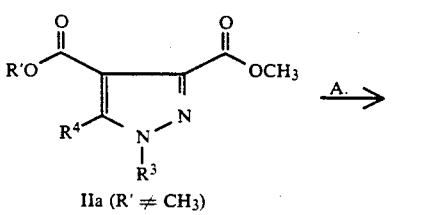

IIa (R' ≠ $CH_3$)

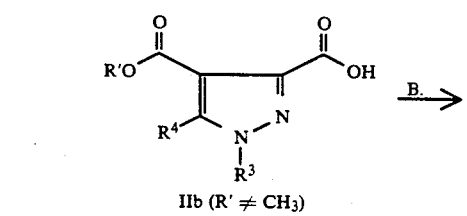

IIb (R' ≠ $CH_3$)

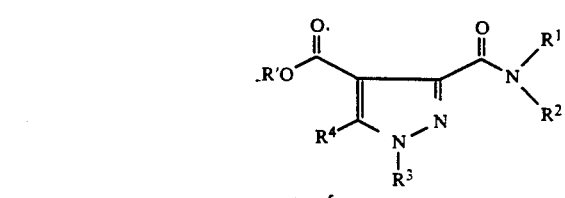

I ($R^5$ = $CO_2R'$; R' ≠ $CH_3$)

R' is $C_1$–$C_4$-alkyl, such as methyl, ethyl, propyl, iso-propyl, n-butyl or sec-butyl, preferably ethyl or iso-propyl.

The reaction is carried out by reacting a pyrazoledicarboxylate IIa in an inert solvent with an aqueous base at from −30° C. to 120° C., preferably from −10° C. to 40° C. The pyrazolemonocarboxylic acid of the formula IIa is then liberated at from −30° C. to 100° C., preferably from −10° C. to 10° C., by adding a mineral acid.

Suitable solvents are alcohols, such as methanol, ethanol, propanol or ethylene glycol, preferably the alcohol which corresponds to the ester component in II. The concentration of the starting material II is generally from 0.1 to 0.5 mol/l, preferably from 0.2 to 2.0 mol/l.

The aqueous base employed is a 5 to 20% strength aqueous solution of an alkali metal hydroxide or alkaline earth metal hydroxide, such as LiOH, NaOH, KOH, $Ca(OH)_2$ or $Ba(OH)_2$, preferably NaOH or KOH.

The molar ratio between the diester IIa and hydroxide is from 1:0.95 to 1:1 for an alkali metal hydroxide and from 1:0.48 to 1:0.55 for an alkaline earth metal hydroxide.

The reaction is generally complete after 14 hours. The monocarboxylic acid IIb is then liberated by adding a strong mineral acid such as hydrochloric acid or sulfuric acid and isolated in a conventional manner, for example by suction filtration or extraction with an organic solvent.

For conversion into the acyl halide, the carboxylic acid IIb is reacted with a halogenating agent, preferably an inorganic acid halide, if desired in an inert solvent, with addition of a catalytic amount of N,N-dimethylformamide or 4-N,N-dimethylaminopyridine, at from 0° C. to the boiling point of the solvent (mixture) or halogenating agent used.

Suitable inert solvents are halogenated hydrocarbons, such as tetrachloroethane, methylene chloride, chloroform, dichloroethane, chlorobenzene and 1,2-dichlorobenzene, or aromatic compounds, such as benzene, toluene or zylene, preferably benzene or toluene.

Expedient halogenating agents are inorganic acid halides, such as thionyl chloride, phosphorus trichloride or phosphorus pentachloride. The carboxylic acid III and halogenating agent are employed in a ratio of from 1:1 to 1:10, preferably from 1:1 to 1:5. The concentration of the catalyst (N,N-dimethylformamide or 4-N,N-dimethylaminopyridine) is from 1 to 20 mol-%, preferably from 1 to 5 mol-%, based on the carboxylic acid IIb employed.

If the reaction is carried out in a solvent, the concentration of the starting material IIb is from 0.1 to 5.0 mol/l, preferably from 0.2 to 2.0 mol/l.

The process is particularly preferably carried out using five equivalents of thionyl chloride in the presence of 2 mol-% of N,N-dimethylformamide at the reflux temperature of the reaction mixture.

The reaction is generally complete after 5 hours; the acyl chloride IV can be isolated in a conventional manner, for example by removing the excess inorganic acid halide and solvent by distillation and subsequently distilling the acyl halide which remains, if necessary under reduced pressure.

The amide I is obtained in a conventional manner by reacting a pyrazole-3-carbonyl chloride of the formula IV with an amine V. An expedient procedure is to react a solution of the acyl halide in an inert solvent with an amine III, likewise in an inert solvent. The acyl chloride and the amine III are expediently employed in a ratio of from 1:2 to 1:5, but it is also possible to carry out the reaction in the presence of an acid acceptor, in which case the acyl chloride and the amine III are expediently employed in a ratio of from 1:1 to 1:1.5 and the acyl chloride and the acid acceptor in a ratio of from 1:1.5 to 1:5.

The solvent used for these reactions is preferably a halogenated hydrocarbon, such as tetrachloroethane, methylene chloride, chloroform, dichloroethane, chlorobenzene or 1,2-dichlorobenzene, or an ether, e.g. diethyl ether, methyl tert-butyl ether, 1,2-dimethoxyethane, diethylene glycol dimethyl ether, tetrahydrofuran or dioxane; a dipolar aprotic solvent, e.g. acetonitrile, dimethylformamide, dimethylacetamide, dimethyl sulfoxide, N-methylpyrrolidone, 1,3-dimethyltetrahydro-2(1H)-pyrimidinone or 1,3-dimethylimidazolin-2-one; an aromatic compound, e.g. benzene, toluene or xylene, or a ketone, such as acetone or methyl ethyl ketone. The concentration from 0.1 to 5.0 mol/l, preferably from 0.2 to 2.0 mol/l.

The reaction can be carried out at from −30° C. to the reflux temperature of the solvent (mixture) used.

Preferred acid acceptors are aromatic nitrogen bases, such as pyridine, 4-dimethylaminopyridine and quinoline; tertiary aliphatic amines, such as triethylamine, N-ethyldiisopropylamine and N-methylmorpholine; bicyclic and tricyclic amines, such as diazabicyclooctane (DABCO) and diazabicycloundecane (DBU); and carbonates or bicarbonates of alkali metals or of alkaline earth metals, e.g. sodium carbonate, potassium carbonate, sodium bicarbonate and potassium bicarbonate. It may in some cases also be useful to use combinations of the abovementioned bases.

The process is particularly preferably carried out at from 0° to 30° C. in a halogenated hydrocarbon, such as tetrachloroethane, methylene chloride, chloroform or dichloroethane, in the presence of three equivalents of the amine III. The reaction is generally complete after 14 hours; the mixture can be worked up in a conventional manner, for example by hydrolysis using water and extraction of the amide VI with an organic solvent. The product of formula VI can be purified as usual by recrystallization or chromatography.

2. A process for the preparation of a compound I in which $R^5$ is $CO_2H$

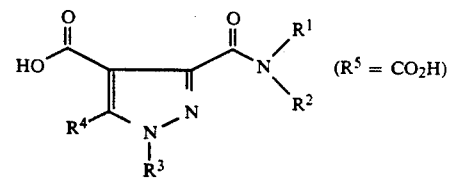

This compound I is obtained by hydrolyzing a pyrazole-3-carboxamide I in which $R^5$ is $CO_2R'$ and $R'$ is $C_1$–$C_4$-alkyl, in a conventional manner in the presence of an aqueous base.

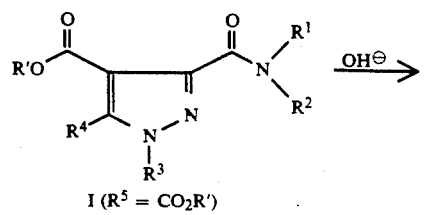

R' in the formula I is as defined above in the case of process 1, but is preferably methyl.

The reaction is carried out by reacting a pyrazolecarboxylate I ($R^5=CO_2R'$) in an inert solvent with an aqueous base at from −30° to 120° C., preferably from 10° to 80° C. The pyrazolecarboxylic acid of the formula I ($R^5=CO_2H$) is then liberated at from −30° to 100° C., preferably from −10° to 10° C., by adding a mineral acid.

Suitable solvents are alcohols, such as methanol, ethanol, propanol and ethylene glycol.

The concentration of the starting material I is generally from 0.1 to 5.0 mol/l, preferably from 0.2 to 2.0 mol/l.

The aqueous base employed is a 5 to 20% strength aqueous solution of an alkali metal hydroxide or of an alkaline earth metal hydroxide, such as LiOH, NaOH, KOH, Ca(OH)$_2$ or Ba(OH)$_2$, preferably NaOH or KOH.

The molar ratio between the ester I and the hydroxide is from 1:0.95 to 1:1.1 for an alkali metal hydroxide and from 1:0.48 to 1:0.55 for an alkaline earth metal hydroxide.

3. A process for the preparation of a compound I in which $R^5$ is $COYR^6$

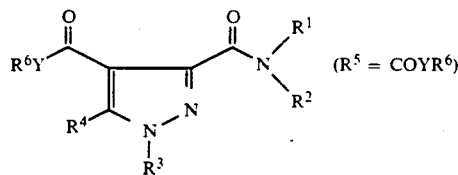

This compound is obtained, for example, by converting a pyrazole-3-carboxamide I in which $R^5$ is $CO_2H$ in a conventional manner into an activated form of the carboxylic acid, and subsequently esterifying the latter using a compound IV.

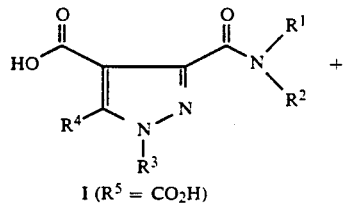

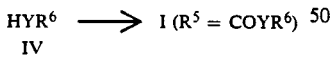

This reaction is usually carried out at from −20° to 60° C., preferably from 0° to 40° C.

The solvent used is expediently a halogenated hydrocarbon, such as tetrachloromethane, methylene chloride, chloroform, dichloroethane, chlorobenzene or 1,2-dichlorobenzene, an ether, e.g. methyl tert-butyl ether, 1,2-dimethoxyethane, diethylene glycol dimethyl ether, tetrahydrofuran or dioxane; a dipolar aprotic solvent, e.g. acetonitrile, dimethylformamide, dimethylacetamide, dimethyl sulfoxide, N-methylpyrrolidone, 1,3-dimethyltetrahydro-2(1H)-pyrimidinone or 1,3-dimethylimidazolin-2-one, or an aromatic compound, e.g. benzene, toluene or xylene. The concentration of the starting materials in the solvent is generally from 0.1 to 5.0mol/l, preferably from 0.2 to 2.0 mol/l.

In general, from 1 to 1.5 mol equivalents, preferably from 1 to 1.15 mol equivalents, of the compound IV are employed, based on the carboxylic acid I ($R^5=CO_2H$).

Suitable dehydrating agents are diimides, such as dicyclohexylcarbodiimide, or anhydrides, such as propanephosphonic anhydride. The reaction is also successful in the presence of 1-methyl-2-halopyridinium iodides as the dehydrating agent (cf. Chem. Lett., (1975) 1045; ibid., (1976), 13; ibid., (1976), 49.

The process is particularly preferably carried out at from 20° to 40° C. in an inert solvent, such as tetrahydrofuran, dichloromethane or toluene, in the presence of dicyclohexylcarbodiimide as the dehydrating agent, the carboxylic acid I, the compound IV and the dehydrating agent being employed in stoichiometric amounts.

The reaction is generally complete after 14 hours; the pyrazole-3-carboxamide is isolated in a conventional manner (for example by diluting the reaction mixture with water and extracting the product with an organic solvent) and purified by conventional standard methods, such as recrystallization or chromatography.

4. A process for the preparation of a compound I in which $R^5$ is 4,5-dihydrooxazol-2-yl

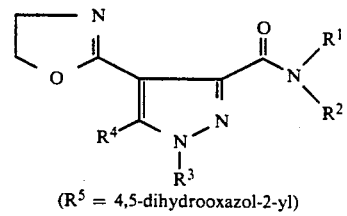

This compound is obtained by reacting a pyrazole-3-carboxamide I in which $R^5$ is $CO_2R'$ or COOH and R' is $C_1$-$C_4$-alkyl in a conventional manner with an amino alcohol of formula V.

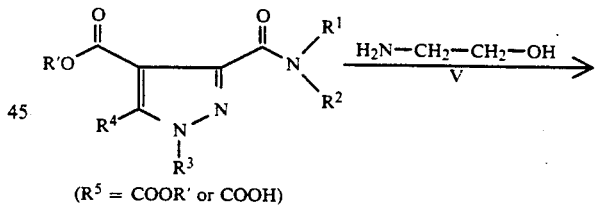

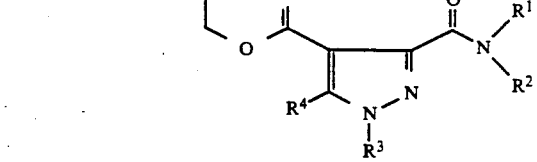

The reaction is carried out by reacting the compound at from 0° to 180° C., preferably at the reflux temperature of the mixture used, with an aminoalcohol V, if desired in the presence of an inert solvent. The ester or carboxylic acid I and the aminoalcohol V are employed in a ratio of from 1:1 to 1:2.5, preferably from 1:1 to 1:1.5.

The solvent used is expediently a halogenated hydrocarbon, such as chlorobenzene or 1,2-dichlorobenzene, an ether, e.g. methyl tert-butyl ether, 1,2-dimethoxyethane, diethylene glycol dimethyl ether, tetrahydrofuran or dioxane; an alcohol, such as methanol, ethanol, propanol or ethylene glycol, a dipolar aprotic solvent, e.g. acetonitrile, dimethylformamide, dimethylacetamide, dimethyl sulfoxide, N-methylpyrrolidone, 1,3-dimethyltetrahydro-2(1H)-pyrimidinone or 1,3-dimethylimidazolin-2-one, or an aromatic compound, e.g. benzene, toluene or xylene. The concentration of the starting materials in the solvent is generally from 0.1 to 5.0 mol/l, preferably from 0.2 to 2.0 mol/l.

The reaction is generally complete after 14 hours; the pyrazolecarboxamide I is then precipitated, if necessary, by adding water, filtered off with suction or extracted with an organic solvent and purified by conventional standard methods, such as recrystallization or chromatography.

With respect to the intended use of the compounds I, preferred substituents are the following radicals:

$R^1$ is hydrogen; $C_3$–$C_8$-cycloalkyl, such as cyclopropyl, cyclobutyl, cyclopentyl, cyclohexyl, cycloheptyl or cyclooctyl, in particular cyclopropyl, cyclobutyl, cyclopentyl or cyclohexyl, which may carry from one to three of the following radicals: halogen, such as fluorine, chlorine, bromine or iodine, in particular fluorine or chlorine; alkyl, such as methyl, ethyl, propyl, 1-methylethyl, butyl, 1-methylpropyl, 2-methylpropyl or 1,1-dimethylethyl, in particular methyl and ethyl; haloalkyl such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethy-1,2-chloro-2,2-difluoroethy-1,2,2-dichloro-2-fluoroethyl, 2,2,2-trichloroethyl or pentafluoroethyl, in particular trifluoromethyl; alkoxy such as methoxy, ethoxy, n-propoxy, 2-methylethoxy, n-butoxy, 1-methylpropoxy, 2-methylpropoxy or 1,1-dimethylethoxy, in particular methoxy or ethoxy,; haloalkoxy, such as difluoromethoxy, trifluoromethoxy, chlorodifluormethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy;

alkyl as mentioned above, and pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethypropyl, 1-ethyl-1-methylpropyl or 1-ethyl-2-methylpropyl, in particular methyl, ethyl, 1-methylethyl or 1,1-dimethylethyl, which may carry from one to three of the following radicals: hydroxyl; halogen as mentioned above, in particular fluorine or chlorine; alkoxy as mentioned above, in particular methoxy or ethoxy; haloalkoxy a mentioned above, in particular trifluoromethoxy; alkylthio, such as methylthio, ethylthio, n-propylthio, 1-methylethylthio, n-butylthio, 1-methylpropylthio, 2-methylpropylthio or 1,1-dimethylethylthio, in particular methylthio or ethylthio; haloalkylthio such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio or pentafluoroethylthio, in particular trifluoromethylthio or pentafluoroethylthio; hydroxycarbonyl; alkoxyisopropyloxycarbonyl; alkylamino such as methylamino, ethylamino, propylamino, isopropylamino, in particular methylamino; dialkylamino such as dimethylamino, diethylamino, dipropylamino, diisopropylamino, methylethylamino, in particular dimethylamino; cycloalkylamino such as cyclopropylamino, cycylobutylamino, cyclopentylamino or cyclohexylamino, in particular cyclopropylamino; and/or a radical

where

R is cyano; nitro; halogen such as, in particular, fluorine or chlorine; alkyl such as, in particular, methyl, ethyl or 1-methylethyl; haloalkyl such as, in particular, trifluoroethyl; alkoxy such as, in particular, methoxy, ethoxy or 1-methylethoxy; haloalkoxy such as, in particular, difluoromethoxy or trifluoromethoxy; alkylthio such as, in particular, methylthio or ethylthio; haloalkylthio such as, in particular, difluoromethylthio or trifluoromethylthio and/or alkoxycarbonyl such as methoxycarbonyl, ethoxycarbonyl, propyloxycarbonyl, 1-methylethoxycarbonyl, butoxycarbonyl, 1-methylpropoxycarbonyl, 2-methylpropoxycarbonyl or 1,1-dimethyl ethoxycarbonyl, in particular methoxycarbonyl or ethoxycarbonyl, m is 0, 1, 2 or 3, it being possible for the radicals R to be different from one another if m is 2 or 3;

$R^2$ is hydroxyl; amino;

alkylamino, such as, in particular, methylamino or ethylamino;

dialkylamino, such as, in particular, dimethylamino or diethylamino; alkyl as mentioned in the case of R and carrying an aminocarbonyl group;

alkoxy, such as, in particular, methoxy or ethoxy, which may carry a radical

alkenyl, such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1,1-dimethyl-2-butenyl,1,1-dimethyl-3-butenyl, 1,2-dimethyl-2-butenyl, 1,2-dimethyl-3-butenyl, 1,3-dimethyl-2-butenyl, 1,3-dimethyl-3-buteny1,2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-buteny1,2-ethyl-3-butenyl, 1,1,2-trimethyl-2-propenyl, 1-ethyl-1-methyl-2-propenyl or 1-ethyl-2-methyl-2-propenyl;

alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

in particular 2-propenyl or 2-propynyl, or phenyl or naphthyl, it being possible for these groups to carry from one to three of the radicals mentioned in general and specific terms in the case of R;

a 5- to 6-membered heterocyclic ring containing one or two heteroatoms selected from the group comprising nitrogen, oxygen and sulfur, such as 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 4-pyrrolyl, 3-pyrazolyl, 4-pyrazolyl, 5-pyrazolyl, 2-pyridyl, 3-pyridyl, 4-pyridyl or 2-(4,6-dimethylpyrimidinyl), it being possible for this ring to contain one or two of the following radicals: halogen, alkyl, haloalkyl, alkoxy, haloalkoxy and/or alkylthio as mentioned in general and specific terms in the case of $R^1$; one of the groups mentioned in general or specific terms in the case of $R^1$, or $R^1$ and $R^2$ together are a 4- to 7-membered chain which may contain one of the following groups as a ring member in addition to methylene groups: oxygen, sulfur, $N(CH_3)$— or —CO—, such as —$(CH_2)_3$—, —$(CH_2)_4$—, —$(CH_2)_5$—, $(CH_2)_6$—, —$CH_2$—O—$CH_2$—, —$CH_2$—$CH_2$—O—$CH_2$—$CH_2$—, —$CH_2$—S—$CH_2$—, —$CH_2$—$CH_2$—S—$CH_2$—$CH_2$—, —$CH_2$—$CH_2$—$N(CH_3)$—$CH_2$—$CH_2$ or —$(CH_2)_3$—CO—, in particular —$(CH_2)_5$— or —$CH_2$—$CH_2$—O—$CH_2$—$CH_2$;

$R^3$ is a 5- to 6-membered heterocyclic ring containing one or two heteroatoms taken from the group comprising oxygen, sulfur and nitrogen, as mentioned in the case of $R^2$, it being possible for this ring to carry one or two of the following radicals: halogen, such as, in particular, fluorine or chlorine, alkyl, such as, in particular, methyl, haloalkyl, such as, in particular, trifluoromethyl or chlorodifluoromethyl, alkoxy, such as, in particular, methoxy or ethoxy, haloalkoxy, such as, in particular, trifluoromethoxy, trichloromethoxy or pentafluoroethoxy, alkylthio, such as, in particular, methylthio, and/or haloalkylthio, such as, in particular, trifluoromethylthio;

alkenyl as mentioned in the case of $R^2$, in particular 2-propenyl, alkynyl as mentioned in the case of $R^2$, in particular 2-propynyl, or phenyl, it being possible for these groups to carry from one to three of the radicals mentioned in general and specific terms in the case of R, or one of the groups mentioned in general or specific terms in the case of $R^1$;

$R^4$ is nitro; cyano; carboxyl;

halogen, such as, in particular, fluorine, chlorine or bromine;

alkoxy or alkylthio, such as, in particular, methoxy, ethoxy, methylthio or ethylthio, it being possible for these groups to carry from one to nine halogen atoms, such as, in particular, fluorine or chlorine;

or one of the groups mentioned in general or specific terms in the case of $R^3$, it being possible for phenyl and alkynyl in this position also to have the following meanings:

ethenyl, 1-propenyl, 1-methylethenyl, 1-butenyl, 1-methyl-1-propenyl, 2-methyl-1-propenyl, 1-pentenyl, 1-methyl-1-butenyl, 2-methyl-1-butenyl, 1,1-dimethyl-1propenyl, 1-ethyl-1-propenyl, 1-hexenyl, 1-methyl-1-pentenyl, 2-methyl-1-pentenyl, 3-methyl-1-pentenyl, 4-methyl-1-pentenyl, 1,2-dimethyl-1-butenyl, 1,3-dimethyl-1-butenyl,1,2-dimethyl-1-butenyl,3,3-dimethyl-1-butenyl, 1-ethyl-1-butenyl, 2-ethyl-1-butenyl, 1-ethyl-2-methyl-1-propenyl, ethynyl, 1-propynyl, 1-butynyl, 1-pentynyl, 3-methyl-1-butynyl, 1-hexynyl, 3-methyl-1-pentynyl, 4-methyl-1-pentynyl or 3,3-dimethyl-1-butynyl;

$R^5$ is 4,5-dihydrooxazol-2-yl or $COYR^6$;

Y is oxygen or sulfur;

$R^6$ is hydrogen;

cycloalkyl as mentioned in the case of $R^1$, in particular cyclopentyl or cyclohexyl;

alkyl as mentioned in the case of $R^1$, in particular methyl, ethyl, propyl, 1-methylethyl or hexyl, which may carry from one to five halogen atoms, such as, in particular, fluorine or chlorine, or hydroxyl groups and/or one of the following radicals: cyano, aminocarbonyl, carboxyl, trimethylsilyl, alkoxy, such as, in particular, methoxy or ethoxy, alkoxyalkoxy, such as methoxyethoxy, ethoxyethoxy or propyloxyethoxy, in particular methoxyethoxy, alkylthio, such as, in particular, methylthio or ethylthio; alkylamino, such as, in particular, methylamino or ethylamino, dialkylamino, such as, in particular, dimethylthio or methylethylamino, alkylsulfinyl, such as methylsulfinyl, ethylsulfinyl, propylsulfinyl, isopropylsulfinyl, in particular methylsulfinyl or ethylsulfinyl; aklylsulfonyl such as methylsulfonyl; ethylsulfonyl, propylsulfonyl or isopropylsulfonyl, in particular methylsulfonyl or ethylsulfonyl; alkoxycarbonyl, such as, in particular, methoxycarbonyl; alkylaminocarbonyl such as methylaminocarbonyl, ethylaminocarbonyl, propylaminocarbonyl or isopropylaminocarbonyl, in particular methylaminocarbonyl or ethylaminocarbonyl; dialkylaminocarbonyl, such as dimethylaminocarbonyl, diethylaminocarbonyl,dipropylaminocarbonyl,diisopropylaminocarbonyl, dicyclopropylaminocarbonyl or methylethylaminocarbonyl, in particular dimethylaminocarbonyl or diethylaminocarbonyl; dialkoxyphosphonyl, such as dimethoxyphosphonyl, diethoxyphosphonyl, dipropoxyphosphonyl or diisopropoxyphosphonyl, in particular dimethoxyphosphonyl or diethoxyphosphonyl; alkaniminooxy, such as, in particular, 2-propaniminoxy; phenyl, thienyl, benzyloxy, benzylthio, furyl, tetrahydrofuryl, phthalimido and/or benzoyl, it being possible for the cyclic radicals to themselves carry from one to three of the radicals mentioned in general or specific terms in the case of R;

alkenyl, such as, in particular, 2-propenyl or 2-butenyl, alkynyl, such as, in particular, 2-propynyl, or cycloalkenyl, such as, in particular, 2-cyclopentenyl or 2-cyclohexenyl, it being possible for these groups to carry one of the following radicals: hydroxyl, halogen, such as, in particular, fluorine or chlorine, alkoxy, such as, in particular, methoxy or ethoxy, or phenyl, which may itself carry from one to three of the radicals mentioned in general or specific terms in the case of R;

a 5- to 6-membered heterocyclic ring containing one or two heteroatoms selected from the group comprising nitrogen, oxygen and sulfur, as mentioned in the case of $R^2$, in particular tetrahydrofuranyl or tetrahydropyranyl;

phthalimido; tetrahydrophthalimido; succinimido; maleiimido; benzotriazolyl;

phenyl which may carry from one to three of the radicals mentioned in general or specific terms in the case of R;

$N=CR^7R^8$ where $R^7$ is hydrogen or alkyl as mentioned in the case of $R^1$, in particular methyl, ethyl or 1-methylethyl, and $R^8$ is cycloalkyl, such as, in particular, cyclopropyl, phenyl, furyl or one of the groups mentioned in the case of $R^7$, or $R^7$ and $R^8$ together form an alkylene chain, such as butylene, pentylene, hexylene or heptylene, in particular butylene or pentylene, and agriculturally useful salts thereof.

Particularly preferred compounds I or Ia are those in which $R^1$ and $R^4$ are hydrogen, and compounds I and Ia where $R^1$ is hydrogen;

$R^2$ is alkyl, such as, in particular, methyl, ethyl, propyl, 1-methylethyl or 1,1-dimethylethyl, or cycloalkyl, such as, in particular, cyclopropyl, cyclopentyl or cyclohexyl;

$R^3$ is hydrogen;

alkyl, such as, in particular, methyl, ethyl, propyl or 1-methylethyl, or phenyl which may carry from one to three of the following radicals: halogen, such as, in particular, fluorine or chlorine, alkyl, such as, in particular, methyl, ethyl or 1-methylethyl, haloalkyl, such as, in particular, trifluoromethyl, haloalkoxy, such as, in particular, trifluoromethoxy, alkylthio, such as, in particular, methylthio, and/or haloalkylthio, such as, in particular, trifluoromethylthio;

$R^4$ is hydrogen;

$R^5$ is $COYR^6$;

Y is oxygen;

$R^6$ is hydrogen or $-N=R^7R^8$, and $R^7$ is hydrogen or alkyl, as mentioned in general or specific terms in the case of $R^3$;

$R^8$ is cycloalkyl, as mentioned in specific terms in the case of $R^2$, or one of the groups mentioned in the case of $R^7$, or $R^7$ and $R^8$ together are an alkylene chain, such as, in particular, butylene or pentylene.

Examples of particularly preferred pyrazole-3-carboxamides of general formula Ia are listed in the table below.

TABLE

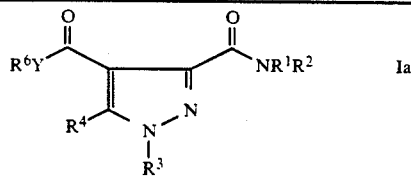

Ia

| $R^3$ | $R^4$ | $R^1$ | $R^2$ | Y | $R^6$ |
|---|---|---|---|---|---|
| methyl | H | H | tert.-butyl | O | H |
| ethyl | H | H | tert.-butyl | O | H |
| n-propyl | H | H | tert.-butyl | O | H |
| iso-propyl | H | H | tert.-butyl | O | H |
| n-butyl | H | H | tert.-butyl | O | H |
| iso-butyl | H | H | tert.-butyl | O | H |
| sec.-butyl | H | H | tert.-butyl | O | H |
| tert.-butyl | H | H | tert.-butyl | O | H |
| cyclo-pentyl | H | H | tert.-butyl | O | H |
| cyclo-hexyl | H | H | tert.-butyl | O | H |
| cyclo-heptyl | H | H | tert.-butyl | O | H |
| cyclo-octyl | H | H | tert.-butyl | O | H |
| 2-methoxy-ethyl | H | H | tert.-butyl | O | H |
| ethoxycarbonyl-methyl | H | H | tert.-butyl | O | H |
| 2,2,2-trifluoroethyl | H | H | tert.-butyl | O | H |
| 2,2,2-trichloroethyl | H | H | tert.-butyl | O | H |
| allyl | H | H | tert.-butyl | O | H |
| methallyl | H | H | tert.-butyl | O | H |
| crotyl | H | H | tert.-butyl | O | H |
| cinnamyl | H | H | tert.-butyl | O | H |
| 3-(4-F-phenyl)-propenyl | H | H | tert.-butyl | O | H |
| 2-butynyl | H | H | tert.-butyl | O | H |
| propargyl | H | H | tert.-butyl | O | H |
| 3-phenyl-2-propynyl | H | H | tert.-butyl | O | H |
| phenyl | H | H | tert.-butyl | O | H |
| 4-F-phenyl | H | H | tert.-butyl | O | H |
| 3-F-phenyl | H | H | tert.-butyl | O | H |
| 2-F-phenyl | H | H | tert.-butyl | O | H |
| 4-Cl-phenyl | H | H | tert.-butyl | O | H |
| 2-Cl-phenyl | H | H | tert.-butyl | O | H |
| 2,4-(Cl,Cl)-phenyl | H | H | tert.-butyl | O | H |
| 2,4-(F,Cl)-phenyl | H | H | tert.-butyl | O | H |
| 2,4,6-(Cl,Cl,Cl)-phenyl | H | H | tert.-butyl | O | H |
| 4-$CF_3$-phenyl | H | H | tert.-butyl | O | H |
| 3-$CF_3$-phenyl | H | H | tert.-butyl | O | H |
| 2,4,6-(Cl,$CF_3$Cl)-phenyl | H | H | tert.-butyl | O | H |
| 2,4,6-(F,$CF_3$,F)-phenyl | H | H | tert.-butyl | O | H |

TABLE-continued

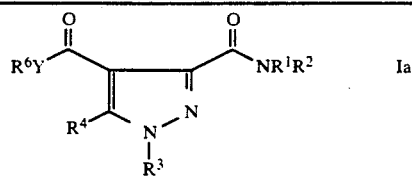

| R³ | R⁴ | R¹ | R² | Y | R⁶ |
|---|---|---|---|---|---|
| 4-NO₂-phenyl | H | H | tert.-butyl | O | H |
| 2-NO₂-phenyl | H | H | tert.-butyl | O | H |
| 4-CCl₃-phenyl | H | H | tert.-butyl | O | H |
| 4-CH₃-phenyl | H | H | tert.-butyl | O | H |
| 2,4,6-trimethylphenyl | H | H | tert.-butyl | O | H |
| 4-t-butylphenyl | H | H | tert.-butyl | O | H |
| 2-iso-propylphenyl | H | H | tert.-butyl | O | H |
| 4-iso-propylphenyl | H | H | tert.-butyl | O | H |
| 4-propylphenyl | H | H | tert.-butyl | O | H |
| 4-CN-phenyl | H | H | tert.-butyl | O | H |
| 3-CN-phenyl | H | H | tert.-butyl | O | H |
| 2-CF₃-phenyl | H | H | tert.-butyl | O | H |
| 2-OCH₃-phenyl | H | H | tert.-butyl | O | H |
| 4-OCH₃-phenyl | H | H | tert.-butyl | O | H |
| 2,4-(OCH₃,OCH₃)-phenyl | H | H | tert.-butyl | O | H |
| 2-SCF₃-phenyl | H | H | tert.-butyl | O | H |
| 4-SCF₃-phenyl | H | H | tert.-butyl | O | H |
| 3-OCF₃-phenyl | H | H | tert.-butyl | O | H |
| 3-OCClF₂-phenyl | H | H | tert.-butyl | O | H |
| 4-OCHF₂-phenyl | H | H | tert.-butyl | O | H |
| 2-SCH₃-phenyl | H | H | tert.-butyl | O | H |
| 4-SCH₃-phenyl | H | H | tert.-butyl | O | H |
| tetrahydronaphthyl | H | H | tert.-butyl | O | H |
| 2,4-(Cl,Cl)-benzyl | H | H | tert.-butyl | O | H |
| 2-thienyl | H | H | tert.-butyl | O | H |
| 3-furanyl | H | H | tert.-butyl | O | H |
| 3-pyridyl | H | H | tert.-butyl | O | H |
| 2-tetrahydropyranyl | H | H | tert.-butyl | O | H |
| 2-pyridyl | H | H | tert.-butyl | O | H |
| 2-ethoxyethyl | H | H | tert.-butyl | O | H |
| 2-methyl-3-pyridyl | H | H | tert.-butyl | O | H |
| methyl | H | H | cyclo-propyl | O | H |
| ethyl | H | H | cyclo-propyl | O | H |
| n-propyl | H | H | cyclo-propyl | O | H |
| iso-propyl | H | H | cyclo-propyl | O | H |
| n-butyl | H | H | cyclo-propyl | O | H |
| iso-butyl | H | H | cyclo-propyl | O | H |
| sec.-butyl | H | H | cyclo-propyl | O | H |
| tert.-butyl | H | H | cyclo-propyl | O | H |
| cyclo-pentyl | H | H | cyclo-propyl | O | H |
| cyclo-hexyl | H | H | cyclo-propyl | O | H |
| cyclo-heptyl | H | H | cyclo-propyl | O | H |
| cyclo-octyl | H | H | cyclo-propyl | O | H |
| 2-methoxy-ethyl | H | H | cyclo-propyl | O | H |
| ethoxycarbonyl-methyl | H | H | cyclo-propyl | O | H |
| 2,2,2-trifluoroethyl | H | H | cyclo-propyl | O | H |
| 2,2,2-trichloroethyl | H | H | cyclo-propyl | O | H |
| allyl | H | H | cyclo-propyl | O | H |
| methallyl | H | H | cyclo-propyl | O | H |
| crotyl | H | H | cyclo-propyl | O | H |
| cinnamyl | H | H | cyclo-propyl | O | H |
| 3-(4-F-phenyl)-propenyl | H | H | cyclo-propyl | O | H |
| 2-butynyl | H | H | cyclo-propyl | O | H |
| propargyl | H | H | cyclo-propyl | O | H |
| 3-phenyl-2-propinyl | H | H | cyclo-propyl | O | H |
| phenyl | H | H | cyclo-propyl | O | H |
| 4-F-phenyl | H | H | cyclo-propyl | O | H |
| 3-F-phenyl | H | H | cyclo-propyl | O | H |
| 2-F-phenyl | H | H | cyclo-propyl | O | H |
| 4-Cl-phenyl | H | H | cyclo-propyl | O | H |
| 2-Cl-phenyl | H | H | cyclo-propyl | O | H |
| 2,4-(Cl,Cl)-phenyl | H | H | cyclo-propyl | O | H |
| 2,4-(F,Cl)-phenyl | H | H | cyclo-propyl | O | H |
| 2,4,6-(Cl,Cl,Cl)-phenyl | H | H | cyclo-propyl | O | H |
| 4-CF₃-phenyl | H | H | cyclo-propyl | O | H |
| 3-CF₃-phenyl | H | H | cyclo-propyl | O | H |
| 2,4,6-(Cl,CF₃Cl)-phenyl | H | H | cyclo-propyl | O | H |
| 2,4,6-(F,CF₃,F)-phenyl | H | H | cyclo-propyl | O | H |
| 4-CCl₃-phenyl | H | H | cyclo-propyl | O | H |
| 4-CH₃-phenyl | H | H | cyclo-propyl | O | H |
| 2,4,6-trimethylphenyl | H | H | cyclo-propyl | O | H |
| 4-t-butylphenyl | H | H | cyclo-propyl | O | H |

TABLE-continued

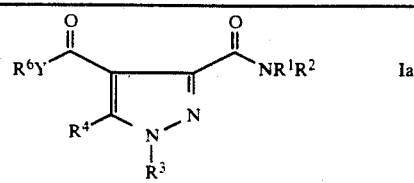

| R³ | R⁴ | R¹ | R² | Y | R⁶ |
|---|---|---|---|---|---|
| 2-iso-propylphenyl | H | H | cyclo-propyl | O | H |
| 4-iso-propylphenyl | H | H | cyclo-propyl | O | H |
| 4-propylphenyl | H | H | cyclo-propyl | O | H |
| 4-CN-phenyl | H | H | cyclo-propyl | O | H |
| 3-CN-phenyl | H | H | cyclo-propyl | O | H |
| 2-CF₃-phenyl | H | H | cyclo-propyl | O | H |
| 2-OCH₃-phenyl | H | H | cyclo-propyl | O | H |
| 4-OCH₃-phenyl | H | H | cyclo-propyl | O | H |
| 2,4-(OCH₃,OCH₃)-phenyl | H | H | cyclo-propyl | O | H |
| 2-SCF₃-phenyl | H | H | cyclo-propyl | O | H |
| 4-SCF₃-phenyl | H | H | cyclo-propyl | O | H |
| 3-OCF₃-phenyl | H | H | cyclo-propyl | O | H |
| 3-OCClF₂-phenyl | H | H | cyclo-propyl | O | H |
| 4-OCHF₂-phenyl | H | H | cyclo-propyl | O | H |
| 2-SCH₃-phenyl | H | H | cyclo-propyl | O | H |
| 4-SCH₃-phenyl | H | H | cyclo-propyl | O | H |
| tetrahydronaphthyl | H | H | cyclo-propyl | O | H |
| 2,4-(Cl,Cl)-benzyl | H | H | cyclo-propyl | O | H |
| 2-thienyl | H | H | cyclo-propyl | O | H |
| 3-furanyl | H | H | cyclo-propyl | O | H |
| 3-pyridyl | H | H | cyclo-propyl | O | H |
| 2-tetrahydropyranyl | H | H | cyclo-propyl | O | H |
| 2-pyridyl | H | H | cyclo-propyl | O | H |
| 2-ethoxyethyl | H | H | cyclo-propyl | O | H |
| 2-methyl-3-pyridyl | H | H | cyclo-propyl | O | H |
| H | H | H | tert.-butyl | O | —N=C(CH₃)₂ |
| methyl | H | H | tert.-butyl | O | —N=C(CH₃)₂ |
| ethyl | H | H | tert.-butyl | O | —N=C(CH₃)₂ |
| n-propyl | H | H | tert.-butyl | O | —N=C(CH₃)₂ |
| iso-propyl | H | H | tert.-butyl | O | —N=C(CH₃)₂ |
| n-butyl | H | H | tert.-butyl | O | —N=C(CH₃)₂ |
| iso-butyl | H | H | tert.-butyl | O | —N=C(CH₃)₂ |
| sec.-butyl | H | H | tert.-butyl | O | —N=C(CH₃)₂ |
| tert.-butyl | H | H | tert.-butyl | O | —N=C(CH₃)₂ |
| cyclo-pentyl | H | H | tert.-butyl | O | —N=C(CH₃)₂ |
| cyclo-hexyl | H | H | tert.-butyl | O | —N=C(CH₃)₂ |
| cyclo-heptyl | H | H | tert.-butyl | O | —N=C(CH₃)₂ |
| cyclo-octyl | H | H | tert.-butyl | O | —N=C(CH₃)₂ |
| 2-methoxy-ethyl | H | H | tert.-butyl | O | —N=C(CH₃)₂ |
| ethoxycarbonyl-methyl | H | H | tert.-butyl | O | —N=C(CH₃)₂ |
| 2,2,2-trifluoroethyl | H | H | tert.-butyl | O | —N=C(CH₃)₂ |
| 2,2,2-trichloroethyl | H | H | tert.-butyl | O | —N=C(CH₃)₂ |
| allyl | H | H | tert.-butyl | O | —N=C(CH₃)₂ |
| methallyl | H | H | tert.-butyl | O | —N=C(CH₃)₂ |
| crotyl | H | H | tert.-butyl | O | —N=C(CH₃)₂ |
| cinnamyl | H | H | tert.-butyl | O | —N=C(CH₃)₂ |
| 3-(4-F-phenyl)-propenyl | H | H | tert.-butyl | O | —N=C(CH₃)₂ |
| 2-butynyl | H | H | tert.-butyl | O | —N=C(CH₃)₂ |
| propargyl | H | H | tert.-butyl | O | —N=C(CH₃)₂ |
| 3-phenyl-2-propynyl | H | H | tert.-butyl | O | —N=C(CH₃)₂ |
| phenyl | H | H | tert.-butyl | O | —N=C(CH₃)₂ |
| 4-F-phenyl | H | H | tert.-butyl | O | —N=C(CH₃)₂ |
| 3-F-phenyl | H | H | tert.-butyl | O | —N=C(CH₃)₂ |
| 2-F-phenyl | H | H | tert.-butyl | O | —N=C(CH₃)₂ |
| 4-Cl-phenyl | H | H | tert.-butyl | O | —N=C(CH₃)₂ |
| 2-Cl-phenyl | H | H | tert.-butyl | O | —N=C(CH₃)₂ |
| 2,4-(Cl,Cl)-phenyl | H | H | tert.-butyl | O | —N=C(CH₃)₂ |
| 2,4-(F,Cl)-phenyl | H | H | tert.-butyl | O | —N=C(CH₃)₂ |
| 2,4,6-(Cl,Cl,Cl)-phenyl | H | H | tert.-butyl | O | —N=C(CH₃)₂ |
| 4-CF₃-phenyl | H | H | tert.-butyl | O | —N=C(CH₃)₂ |
| 3-CF₃-phenyl | H | H | tert.-butyl | O | —N=C(CH₃)₂ |
| 2,4,6-(Cl,CF₃Cl)-phenyl | H | H | tert.-butyl | O | —N=C(CH₃)₂ |
| 2,4,6-(F,CF₃,F)-phenyl | H | H | tert.-butyl | O | —N=C(CH₃)₂ |
| 4-NO₂-phenyl | H | H | tert.-butyl | O | —N=C(CH₃)₂ |
| 2-NO₂-phenyl | H | H | tert.-butyl | O | —N=C(CH₃)₂ |
| 4-CCl₃-phenyl | H | H | tert.-butyl | O | —N=C(CH₃)₂ |
| 4-CH₃-phenyl | H | H | tert.-butyl | O | —N=C(CH₃)₂ |
| 2,4,6-trimethylphenyl | H | H | tert.-butyl | O | —N=C(CH₃)₂ |
| 4-t-butylphenyl | H | H | tert.-butyl | O | —N=C(CH₃)₂ |
| 2-iso-propylphenyl | H | H | tert.-butyl | O | —N=C(CH₃)₂ |
| 4-iso-propylphenyl | H | H | tert.-butyl | O | —N=C(CH₃)₂ |
| 4-propylphenyl | H | H | tert.-butyl | O | —N=C(CH₃)₂ |

TABLE-continued

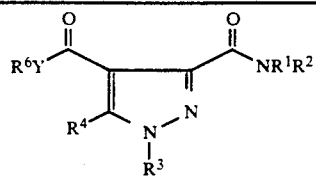

Ia

| R³ | R⁴ | R¹ | R² | Y | R⁶ |
|---|---|---|---|---|---|
| 4-CN-phenyl | H | H | tert.-butyl | O | $-N=C(CH_3)_2$ |
| 3-CN-phenyl | H | H | tert.-butyl | O | $-N=C(CH_3)_2$ |
| 2-CF₃-phenyl | H | H | tert.-butyl | O | $-N=C(CH_3)_2$ |
| 2-OCH₃-phenyl | H | H | tert.-butyl | O | $-N=C(CH_3)_2$ |
| 4-OCH₃-phenyl | H | H | tert.-butyl | O | $-N=C(CH_3)_2$ |
| 2,4-(OCH₃,OCH₃)-phenyl | H | H | tert.-butyl | O | $-N=C(CH_3)_2$ |
| 2-SCF₃-phenyl | H | H | tert.-butyl | O | $-N=C(CH_3)_2$ |
| 4-SCF₃-phenyl | H | H | tert.-butyl | O | $-N=C(CH_3)_2$ |
| 3-OCF₃-phenyl | H | H | tert.-butyl | O | $-N=C(CH_3)_2$ |
| 3-OCClF₂-phenyl | H | H | tert.-butyl | O | $-N=C(CH_3)_2$ |
| 4-OCHF₂-phenyl | H | H | tert.-butyl | O | $-N=C(CH_3)_2$ |
| 2-SCH₃-phenyl | H | H | tert.-butyl | O | $-N=C(CH_3)_2$ |
| 4-SCH₃-phenyl | H | H | tert.-butyl | O | $-N=C(CH_3)_2$ |
| tetrahydronaphthyl | H | H | tert.-butyl | O | $-N=C(CH_3)_2$ |
| 2,4-(Cl,Cl)-benzyl | H | H | tert.-butyl | O | $-N=C(CH_3)_2$ |
| 2-thienyl | H | H | tert.-butyl | O | $-N=C(CH_3)_2$ |
| 3-furanyl | H | H | tert.-butyl | O | $-N=C(CH_3)_2$ |
| 3-pyridyl | H | H | tert.-butyl | O | $-N=C(CH_3)_2$ |
| 2-tetrahydropyranyl | H | H | tert.-butyl | O | $-N=C(CH_3)_2$ |
| 2-pyridyl | H | H | tert.-butyl | O | $-N=C(CH_3)_2$ |
| 2-ethoxyethyl | H | H | tert.-butyl | O | $-N=C(CH_3)_2$ |
| 2-methyl-3-pyridyl | H | H | tert.-butyl | O | $-N=C(CH_3)_2$ |
| H | H | H | cyclo-propyl | O | $-N=C(CH_3)_2$ |
| methyl | H | H | cyclo-propyl | O | $-N=C(CH_3)_2$ |
| ethyl | H | H | cyclo-propyl | O | $-N=C(CH_3)_2$ |
| n-propyl | H | H | cyclo-propyl | O | $-N=C(CH_3)_2$ |
| iso-propyl | H | H | cyclo-propyl | O | $-N=C(CH_3)_2$ |
| n-butyl | H | H | cyclo-propyl | O | $-N=C(CH_3)_2$ |
| iso-butyl | H | H | cyclo-propyl | O | $-N=C(CH_3)_2$ |
| sec.-butyl | H | H | cyclo-propyl | O | $-N=C(CH_3)_2$ |
| tert.-butyl | H | H | cyclo-propyl | O | $-N=C(CH_3)_2$ |
| cyclo-pentyl | H | H | cyclo-propyl | O | $-N=C(CH_3)_2$ |
| cyclo-hexyl | H | H | cyclo-propyl | O | $-N=C(CH_3)_2$ |
| cyclo-heptyl | H | H | cyclo-propyl | O | $-N=C(CH_3)_2$ |
| cyclo-octyl | H | H | cyclo-propyl | O | $-N=C(CH_3)_2$ |
| 2-methoxy-ethyl | H | H | cyclo-propyl | O | $-N=C(CH_3)_2$ |
| ethoxycarbonyl-methyl | H | H | cyclo-propyl | O | $-N=C(CH_3)_2$ |
| 2,2,2-trifluoroethyl | H | H | cyclo-propyl | O | $-N=C(CH_3)_2$ |
| 2,2,2-trichloroethyl | H | H | cyclo-propyl | O | $-N=C(CH_3)_2$ |
| allyl | H | H | cyclo-propyl | O | $-N=C(CH_3)_2$ |
| methallyl | H | H | cyclo-propyl | O | $-N=C(CH_3)_2$ |
| crotyl | H | H | cyclo-propyl | O | $-N=C(CH_3)_2$ |
| cinnamyl | H | H | cyclo-propyl | O | $-N=C(CH_3)_2$ |
| 3-(4-F-phenyl)-propenyl | H | H | cyclo-propyl | O | $-N=C(CH_3)_2$ |
| 2-butynyl | H | H | cyclo-propyl | O | $-N=C(CH_3)_2$ |
| propargyl | H | H | cyclo-propyl | O | $-N=C(CH_3)_2$ |
| 3-phenyl-2-propinyl | H | H | cyclo-propyl | O | $-N=C(CH_3)_2$ |
| phenyl | H | H | cyclo-propyl | O | $-N=C(CH_3)_2$ |
| 4-F-phenyl | H | H | cyclo-propyl | O | $-N=C(CH_3)_2$ |
| 3-F-phenyl | H | H | cyclo-propyl | O | $-N=C(CH_3)_2$ |
| 2-F-phenyl | H | H | cyclo-propyl | O | $-N=C(CH_3)_2$ |
| 4-Cl-phenyl | H | H | cyclo-propyl | O | $-N=C(CH_3)_2$ |
| 2-Cl-phenyl | H | H | cyclo-propyl | O | $-N=C(CH_3)_2$ |
| 2,4-(Cl,Cl)-phenyl | H | H | cyclo-propyl | O | $-N=C(CH_3)_2$ |
| 2,4-(F,Cl)-phenyl | H | H | cyclo-propyl | O | $-N=C(CH_3)_2$ |
| 2,4,6-(Cl,Cl,Cl)-phenyl | H | H | cyclo-propyl | O | $-N=C(CH_3)_2$ |
| 4-CF₃-phenyl | H | H | cyclo-propyl | O | $-N=C(CH_3)_2$ |
| 3-CF₃-phenyl | H | H | cyclo-propyl | O | $-N=C(CH_3)_2$ |
| 2,4,6-(Cl,CF₃Cl)-phenyl | H | H | cyclo-propyl | O | $-N=C(CH_3)_2$ |
| 2,4,6-(F,CF₃,F)-phenyl | H | H | cyclo-propyl | O | $-N=C(CH_3)_2$ |
| 4-CCl₃-phenyl | H | H | cyclo-propyl | O | $-N=C(CH_3)_2$ |
| 4-CH₃-phenyl | H | H | cyclo-propyl | O | $-N=C(CH_3)_2$ |
| 2,4,6-trimethylphenyl | H | H | cyclo-propyl | O | $-N=C(CH_3)_2$ |
| 4-t-butylphenyl | H | H | cyclo-propyl | O | $-N=C(CH_3)_2$ |
| 2-iso-propylphenyl | H | H | cyclo-propyl | O | $-N=C(CH_3)_2$ |
| 4-iso-propylphenyl | H | H | cyclo-propyl | O | $-N=C(CH_3)_2$ |
| 4-propylphenyl | H | H | cyclo-propyl | O | $-N=C(CH_3)_2$ |
| 4-CN-phenyl | H | H | cyclo-propyl | O | $-N=C(CH_3)_2$ |
| 3-CN-phenyl | H | H | cyclo-propyl | O | $-N=C(CH_3)_2$ |
| 2-CF₃-phenyl | H | H | cyclo-propyl | O | $-N=C(CH_3)_2$ |
| 2-OCH₃-phenyl | H | H | cyclo-propyl | O | $-N=C(CH_3)_2$ |
| 4-OCH₃-phenyl | H | H | cyclo-propyl | O | $-N=C(CH_3)_2$ |

TABLE-continued

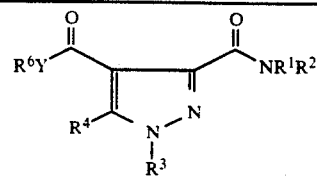

| $R^3$ | $R^4$ | $R^1$ | $R^2$ | Y | $R^6$ |
|---|---|---|---|---|---|
| 2,4-(OCH$_3$,OCH$_3$)-phenyl | H | H | cyclo-propyl | O | $-N=C(CH_3)_2$ |
| 2-SCF$_3$-phenyl | H | H | cyclo-propyl | O | $-N=C(CH_3)_2$ |
| 4-SCF$_3$-phenyl | H | H | cyclo-propyl | O | $-N=C(CH_3)_2$ |
| 3-OCF$_3$-phenyl | H | H | cyclo-propyl | O | $-N=C(CH_3)_2$ |
| 3-OCClF$_2$-phenyl | H | H | cyclo-propyl | O | $-N=C(CH_3)_2$ |
| 4-OCHF$_2$-phenyl | H | H | cyclo-propyl | O | $-N=C(CH_3)_2$ |
| 2-SCH$_3$-phenyl | H | H | cyclo-propyl | O | $-N=C(CH_3)_2$ |
| 4-SCH$_3$-phenyl | H | H | cyclo-propyl | O | $-N=C(CH_3)_2$ |
| tetrahydronaphthyl | H | H | cyclo-propyl | O | $-N=C(CH_3)_2$ |
| 2,4-(Cl,Cl)-benzyl | H | H | cyclo-propyl | O | $-N=C(CH_3)_2$ |
| 2-thienyl | H | H | cyclo-propyl | O | $-N=C(CH_3)_2$ |
| 3-furanyl | H | H | cyclo-propyl | O | $-N=C(CH_3)_2$ |
| 3-pyridyl | H | H | cyclo-propyl | O | $-N=C(CH_3)_2$ |
| 2-tetrahydropyranyl | H | H | cyclo-propyl | O | $-N=C(CH_3)_2$ |
| 2-pyridyl | H | H | cyclo-propyl | O | $-N=C(CH_3)_2$ |
| 2-ethoxyethyl | H | H | cyclo-propyl | O | $-N=C(CH_3)_2$ |
| 2-methyl-3-pyridyl | H | H | cyclo-propyl | O | $-N=C(CH_3)_2$ |
| H | methyl | methyl | tert.-butyl | O | H |
| methyl | methyl | methyl | tert.-butyl | O | H |
| ethyl | methyl | methyl | tert.-butyl | O | H |
| n-propyl | methyl | methyl | tert.-butyl | O | H |
| iso-propyl | methyl | methyl | tert.-butyl | O | H |
| n-butyl | methyl | methyl | tert.-butyl | O | H |
| iso-butyl | methyl | methyl | tert.-butyl | O | H |
| sec.-butyl | methyl | methyl | tert.-butyl | O | H |
| tert.-butyl | methyl | methyl | tert.-butyl | O | H |
| cyclo-pentyl | methyl | methyl | tert.-butyl | O | H |
| cyclo-hexyl | methyl | methyl | tert.-butyl | O | H |
| cyclo-heptyl | methyl | methyl | tert.-butyl | O | H |
| cyclo-octyl | methyl | methyl | tert.-butyl | O | H |
| 2-methoxy-ethyl | methyl | methyl | tert.-butyl | O | H |
| ethoxycarbonyl-methyl | methyl | methyl | tert.-butyl | O | H |
| 2,2,2-trifluoroethyl | methyl | methyl | tert.-butyl | O | H |
| 2,2,2-trichloroethyl | methyl | methyl | tert.-butyl | O | H |
| allyl | methyl | methyl | tert.-butyl | O | H |
| methallyl | methyl | methyl | tert.-butyl | O | H |
| crotyl | methyl | methyl | tert.-butyl | O | H |
| cinnamyl | methyl | methyl | tert.-butyl | O | H |
| 3-(4-F-phenyl)-propenyl | methyl | methyl | tert.-butyl | O | H |
| 2-butynyl | bromo | allyl | tert.-butyl | O | H |
| propargyl | bromo | allyl | tert.-butyl | O | H |
| 3-phenyl-2-propinyl | bromo | allyl | tert.-butyl | O | H |
| phenyl | bromo | allyl | tert.-butyl | O | H |
| 4-F-phenyl | bromo | allyl | tert.-butyl | O | H |
| 3-F-phenyl | bromo | allyl | tert.-butyl | O | H |
| 2-F-phenyl | bromo | allyl | tert.-butyl | O | H |
| 4-Cl-phenyl | bromo | allyl | tert.-butyl | O | H |
| 2-Cl-phenyl | bromo | allyl | tert.-butyl | O | H |
| 2,4-(Cl,Cl)-phenyl | bromo | allyl | tert.-butyl | O | H |
| 2,4-(F,Cl)-phenyl | bromo | allyl | tert.-butyl | O | H |
| 2,4,6-(Cl,Cl,Cl)-phenyl | bromo | allyl | tert.-butyl | O | H |
| 4-CF$_3$-phenyl | bromo | allyl | tert.-butyl | O | H |
| 3-CF$_3$-phenyl | bromo | allyl | tert.-butyl | O | H |
| 2,4,6-(Cl,CF$_3$Cl)-phenyl | bromo | allyl | tert.-butyl | O | H |
| 2,4,6-(F,CF$_3$,F)-phenyl | bromo | allyl | tert.-butyl | O | H |
| 4-NO$_2$-phenyl | bromo | allyl | tert.-butyl | O | H |
| 2-NO$_2$-phenyl | bromo | allyl | tert.-butyl | O | H |
| 4-CCl$_3$-phenyl | bromo | allyl | tert.-butyl | O | H |
| 4-CH$_3$-phenyl | bromo | allyl | tert.-butyl | O | H |
| 2,4,6-trimethylphenyl | bromo | allyl | tert.-butyl | O | H |
| 4-t-butylphenyl | bromo | allyl | tert.-butyl | O | H |
| 2-iso-propylphenyl | bromo | allyl | tert.-butyl | O | H |
| 4-iso-propylphenyl | bromo | allyl | tert.-butyl | O | H |
| 4-propylphenyl | bromo | allyl | tert.-butyl | O - | H |
| 4-CN-phenyl | bromo | allyl | tert.-butyl | O | H |
| 3-CN-phenyl | bromo | allyl | tert.-butyl | O | H |
| 2-CF$_3$-phenyl | bromo | allyl | tert.-butyl | O | H |
| 2-OCH$_3$-phenyl | H | allyl | tert.-butyl | O | H |
| 4-OCH$_3$-phenyl | H | allyl | tert.-butyl | O | H |
| 2,4-(OCH$_3$.OCH$_3$)-phenyl | H | allyl | tert.-butyl | O | H |
| 2-SCF$_3$-phenyl | H | allyl | tert.-butyl | O | H |
| 4-SCF$_3$-phenyl | H | allyl | tert.-butyl | O | H |

TABLE-continued

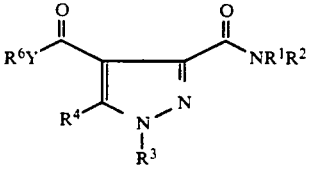

| R³ | R⁴ | R¹ | R² | Y | R⁶ |
|---|---|---|---|---|---|
| 3-OCF₃-phenyl | H | allyl | tert.-butyl | O | H |
| 3-OCClF₂-phenyl | H | allyl | tert.-butyl | O | H |
| 4-OCHF₂-phenyl | H | allyl | tert.-butyl | O | H |
| 2-SCH₃-phenyl | H | allyl | tert.-butyl | O | H |
| 4-SCH₃-phenyl | H | allyl | tert.-butyl | O | H |
| tetrahydronaphthyl | H | allyl | tert.-butyl | O | H |
| 2,4-(Cl,Cl)-benzyl | H | allyl | tert.-butyl | O | H |
| 2-thienyl | H | allyl | tert.-butyl | O | H |
| 3-furanyl | H | allyl | tert.-butyl | O | H |
| 3-pyridyl | H | allyl | tert.-butyl | O | H |
| 2-tetrahydropyranyl | H | allyl | tert.-butyl | O | H |
| 2-pyridyl | H | allyl | tert.-butyl | O | H |
| 2-ethoxyethyl | H | allyl | tert.-butyl | O | H |
| 2-methyl-3-pyridyl | H | allyl | tert.-butyl | O | H |
| H | methyl | methyl | cyclo-propyl | O | H |
| methyl | methyl | methyl | cyclo-propyl | O | H |
| ethyl | methyl | methyl | cyclo-propyl | O | H |
| n-propyl | methyl | methyl | cyclo-propyl | O | H |
| iso-propyl | methyl | methyl | cyclo-propyl | O | H |
| n-butyl | methyl | methyl | cyclo-propyl | O | H |
| iso-butyl | methyl | methyl | cyclo-propyl | O | H |
| sec.-butyl | methyl | methyl | cyclo-propyl | O | H |
| tert.-butyl | methyl | methyl | cyclo-propyl | O | H |
| cyclo-pentyl | bromo | allyl | cyclo-propyl | O | H |
| cyclo-hexyl | bromo | allyl | cyclo-propyl | O | H |
| cyclo-heptyl | bromo | allyl | cyclo-propyl | O | H |
| cyclo-octyl | bromo | allyl | cyclo-propyl | O | H |
| 2-methoxy-ethyl | bromo | allyl | cyclo-propyl | O | H |
| ethoxycarbonyl-methyl | bromo | allyl | cyclo-propyl | O | H |
| 2.2.2-trifluoroethyl | bromo | allyl | cyclo-propyl | O | H |
| 2.2.2-trichloroethyl | bromo | allyl | cyclo-propyl | O | H |
| allyl | bromo | allyl | cyclo-propyl | O | H |
| methallyl | bromo | allyl | cyclo-propyl | O | H |
| crotyl | bromo | allyl | cyclo-propyl | O | H |
| cinnamyl | bromo | allyl | cyclo-propyl | O | H |
| 3-(4-F-phenyl)-propenyl | bromo | allyl | cyclo-propyl | O | H |
| 2-butynyl | bromo | allyl | cyclo-propyl | O | H |
| propargyl | bromo | allyl | cyclo-propyl | O | H |
| 3-phenyl-2-propinyl | bromo | allyl | cyclo-propyl | O | H |
| phenyl | bromo | allyl | cyclo-propyl | O | H |
| 4-F-phenyl | bromo | allyl | cyclo-propyl | O | H |
| 3-F-phenyl | bromo | allyl | cyclo-propyl | O | H |
| 2-F-phenyl | bromo | allyl | cyclo-propyl | O | H |
| 4-Cl-phenyl | bromo | allyl | cyclo-propyl | O | H |
| 2-Cl-phenyl | bromo | allyl | cyclo-propyl | O | H |
| 2,4-(Cl,Cl)-phenyl | bromo | allyl | cyclo-propyl | O | H |
| 2,4-(F,Cl)-phenyl | bromo | allyl | cyclo-propyl | O | H |
| 2,4,6-(Cl,Cl,Cl)-phenyl | bromo | allyl | cyclo-propyl | O | H |
| 4-CF₃-phenyl | bromo | allyl | cyclo-propyl | O | H |
| 3-CF₃-phenyl | bromo | allyl | cyclo-propyl | O | H |
| 2,4,6-(Cl,CF₃Cl)-phenyl | bromo | allyl | cyclo-propyl | O | H |
| 2,4,6-(F,CF₃,F)-phenyl | bromo | allyl | cyclo-propyl | O | H |
| 4-CCl₃-phenyl | methyl | methyl | cyclo-propyl | O | —N=C(CH₃)₂ |
| 4-CH₃-phenyl | methyl | methyl | cyclo-propyl | O | —N=C(CH₃)₂ |
| 2,4,6-trimethylphenyl | methyl | methyl | cyclo-propyl | O | —N=C(CH₃)₂ |
| 4-t-butylphenyl | methyl | methyl | cyclo-propyl | O | —N=C(CH₃)₂ |
| 2-iso-propylphenyl | methyl | methyl | cyclo-propyl | O | —N=C(CH₃)₂ |
| 4-iso-propylphenyl | methyl | methyl | cyclo-propyl | O | —N=C(CH₃)₂ |
| 4-propylphenyl | methyl | methyl | cyclo-propyl | O | —N=C(CH₃)₂ |
| 4-CN-phenyl | methyl | methyl | cyclo-propyl | O | —N=C(CH₃)₂ |
| 3-CN-phenyl | methyl | methyl | cyclo-propyl | O | —N=C(CH₃)₂ |
| 2-CF₃-phenyl | methyl | methyl | cyclo-propyl | O | —N=C(CH₃)₂ |
| 2-OCH₃-phenyl | methyl | methyl | cyclo-propyl | O | —N=C(CH₃)₂ |
| 4-OCH₃-phenyl | methyl | methyl | cyclo-propyl | O | —N=C(CH₃)₂ |
| 2,4-(OCH₃,OCH₃)-phenyl | methyl | methyl | cyclo-propyl | O | —N=C(CH₃)₂ |
| 2-SCF₃-phenyl | methyl | methyl | cyclo-propyl | O | —N=C(CH₃)₂ |
| 4-SCF₃-phenyl | methyl | methyl | cyclo-propyl | O | —N=C(CH₃)₂ |
| 3-OCF₃-phenyl | methyl | methyl | cyclo-propyl | O | —N=C(CH₃)₂ |
| 3-OCClF₂-phenyl | methyl | methyl | cyclo-propyl | O | —N=C(CH₃)₂ |
| 4-OCHF₂-phenyl | methyl | methyl | cyclo-propyl | O | —N=C(CH₃)₂ |
| 2-SCH₃-phenyl | methyl | methyl | cyclo-propyl | O | —N=C(CH₃)₂ |
| 4-SCH₃-phenyl | methyl | methyl | cyclo-propyl | O | —N=C(CH₃)₂ |

TABLE-continued

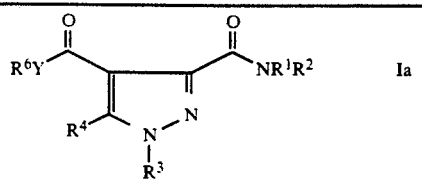

Ia

| R³ | R⁴ | R¹ | R² | Y | R⁶ |
|---|---|---|---|---|---|
| tetrahydronaphthyl | methyl | methyl | cyclo-propyl | O | $-N=C(CH_3)_2$ |
| 2,4-(Cl,Cl)-benzyl | methyl | methyl | cyclo-propyl | O | $-N=C(CH_3)_2$ |
| 2-thienyl | methyl | methyl | cyclo-propyl | O | $-N=C(CH_3)_2$ |
| 3-furanyl | methyl | methyl | cyclo-propyl | O | $-N=C(CH_3)_2$ |
| 3-pyridyl | methyl | methyl | cyclo-propyl | O | $-N=C(CH_3)_2$ |
| 2-tetrahydropyranyl | methyl | methyl | cyclo-propyl | O | $-N=C(CH_3)_2$ |
| 2-pyridyl | methyl | methyl | cyclo-propyl | O | $-N=C(CH_3)_2$ |
| 2-ethoxyethyl | methyl | methyl | cyclo-propyl | O | $-N=C(CH_3)_2$ |
| 2-methyl-3-pyridyl | methyl | methyl | cyclo-propyl | O | $-N=C(CH_3)_2$ |
| H | H | H | tert.-butyl | O | H |
| H | Cl | H | tert.-butyl | O | H |
| H | Br | H | tert.-butyl | O | H |
| H | methyl | H | tert.-butyl | O | H |
| H | ethyl | H | tert.-butyl | O | H |
| methyl | n-propyl | H | tert.-butyl | O | H |
| methyl | iso-propyl | H | tert.-butyl | O | H |
| methyl | n-butyl | H | tert.-butyl | O | H |
| methyl | iso-butyl | H | tert.-butyl | O | H |
| methyl | sec.-butyl | H | tert.-butyl | O | H |
| allyl | tert.-butyl | H | tert.-butyl | O | H |
| allyl | cyclo-propyl | H | tert.-butyl | O | H |
| allyl | cyclo-butyl | H | tert.-butyl | O | H |
| allyl | cyclo-pentyl | H | tert.-butyl | O | H |
| allyl | cyclo-hexyl | H | tert.-butyl | O | H |
| propargyl | cyclo-heptyl | H | tert.-butyl | O | H |
| propargyl | cyclo-octyl | H | tert.-butyl | O | H |
| propargyl | 1-methylcyclopropyl | H | tert.-butyl | O | H |
| propargyl | trifluoromethyl | H | tert.-butyl | O | H |
| propargyl | chlorodifluoromethyl | H | tert.-butyl | O | H |
| 2,2,2-trifluoroethyl | pentafluoroethyl | H | tert.-butyl | O | H |
| 2,2,2-trifluoroethyl | methoxymethyl | H | tert.-butyl | O | H |
| 2,2,2-trifluoroethyl | 1-methylmethoxymethyl | H | tert.-butyl | O | H |
| 2,2,2-trifluoroethyl | 1-methylmethoxyethyl | H | tert.-butyl | O | H |
| 2,2,2-trifluoroethyl | ethoxymethyl | H | tert.-butyl | O | H |
| phenyl | vinyl | H | tert.-butyl | O | H |
| phenyl | allyl | H | tert.-butyl | O | H |
| phenyl | methallyl | H | tert.-butyl | O | H |
| phenyl | crotyl | H | tert.-butyl | O | H |
| phenyl | ethynyl | H | tert.-butyl | O | H |
| 2-F-phenyl | propargyl | H | tert.-butyl | O | H |
| 2-F-phenyl | phenylethynyl | H | tert.-butyl | O | H |
| 2-F-phenyl | methoxy | H | tert.-butyl | O | H |
| 2-F-phenyl | ethoxy | H | tert.-butyl | O | H |
| 2-F-phenyl | iso-propoxy | H | tert.-butyl | O | H |
| 4-F-phenyl | trifluoromethoxy | H | tert.-butyl | O | H |
| 4-F-phenyl | methylthio | H | tert.-butyl | O | H |
| 4-F-phenyl | trifluoromethylthio | H | tert.-butyl | O | H |
| 4-F-phenyl | phenyl | H | tert.-butyl | O | H |
| 4-F-phenyl | 4-F-phenyl | H | tert.-butyl | O | H |
| 2,4,6-(Cl,CF₃Cl)-phenyl | 2-F-phenyl | H | tert.-butyl | O | H |
| 2,4,6-(Cl,CF₃Cl)-phenyl | 2,4-(Cl,Cl)-phenyl | H | tert.-butyl | O | H |
| 2,4,6-(Cl,CF₃Cl)-phenyl | 4-CH₃-phenyl | H | tert.-butyl | O | H |
| 2,4,6-(Cl,CF₃Cl)-phenyl | 4-t-butylphenyl | H | tert.-butyl | O | H |
| 2,4,6-(Cl,CF₃Cl)-phenyl | 2,4-dimethylphenyl | H | tert.-butyl | O | H |
| 2,4,6-(Cl,CF₃Cl)-phenyl | 2,4,6-trimethylphenyl | H | tert.-butyl | O | H |
| 2,4,6-(Cl,CF₃Cl)-phenyl | 2-Cl-phenyl | H | tert.-butyl | O | H |
| 4-CF₃-phenyl | 3-Cl-phenyl | H | tert.-butyl | O | H |
| 4-CF₃-phenyl | 4-Cl-phenyl | H | tert.-butyl | O | H |
| 4-CF₃-phenyl | 4-CN-phenyl | H | tert.-butyl | O | H |
| 4-CF₃-phenyl | nitro | H | tert.-butyl | O | H |
| 4-CF₃-phenyl | COOH | H | tert.-butyl | O | H |
| 4-CF₃-phenyl | 2-CF₃-phenyl | H | tert.-butyl | O | H |
| 4-CF₃-phenyl | 3-CF₃-phenyl | H | tert.-butyl | O | H |
| 4-CF₃-phenyl | 4-CF₃-phenyl | H | tert.-butyl | O | H |
| 4-CF₃-phenyl | 2-OCH₃-phenyl | H | tert.-butyl | O | H |
| 4-CN-phenyl | 3-OCH₃-phenyl | H | tert.-butyl | O | H |
| 4-CN-phenyl | 4-OCH₃-phenyl | H | tert.-butyl | O | H |
| 4-SCF₃-phenyl | s-tert.-butyl | H | tert.-butyl | O | H |
| 4-SCF₃-phenyl | phenylthio | H | tert.-butyl | O | H |
| 4-SCF₃-phenyl | 4-F-phenylthio | H | tert.-butyl | O | H |
| 4-SCF₃-phenyl | S-iso-propyl | H | tert.-butyl | O | H |
| 4-SCF₃-phenyl | 3-pyridyl | H | tert.-butyl | O | H |

TABLE-continued

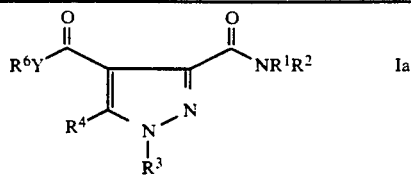

Ia

| R³ | R⁴ | R¹ | R² | Y | R⁶ |
|---|---|---|---|---|---|
| 2-pyridyl | 3-thienyl | H | tert.-butyl | O | H |
| 2-pyridyl | 2-pyridyl | H | tert.-butyl | O | H |
| 2-pyridyl | 2-thienyl | H | tert.-butyl | O | H |
| 2-pyridyl | cinnamyl | H | tert.-butyl | O | H |
| 2-pyridyl | 3-(4-F-phenyl)-propenyl | H | tert.-butyl | O | H |
| 2-pyridyl | 2,4-(NO₂,NO₂)-phenyl | H | tert.-butyl | O | H |
| H | H | H | cyclo-propyl | O | H |
| H | Cl | H | cyclo-propyl | O | H |
| H | Br | H | cyclo-propyl | O | H |
| H | methyl | H | cyclo-propyl | O | H |
| H | ethyl | H | cyclo-propyl | O | H |
| methyl | n-propyl | H | cyclo-propyl | O | H |
| methyl | iso-propyl | H | cyclo-propyl | O | H |
| methyl | n-butyl | H | cyclo-propyl | O | H |
| methyl | iso-butyl | H | cyclo-propyl | O | H |
| methyl | sec.-butyl | H | cyclo-propyl | O | H |
| allyl | tert.-butyl | H | cyclo-propyl | O | H |
| allyl | cyclo-propyl | H | cyclo-propyl | O | H |
| allyl | cyclo-butyl | H | cyclo-propyl | O | H |
| allyl | cyclo-pentyl | H | cyclo-propyl | O | H |
| allyl | cyclo-hexyl | H | cyclo-propyl | O | H |
| propargyl | cyclo-heptyl | H | cyclo-propyl | O | H |
| propargyl | cyclo-octyl | H | cyclo-propyl | O | H |
| propargyl | 1-methylcyclopropyl | H | cyclo-propyl | O | H |
| propargyl | trifluoromethyl | H | cyclo-propyl | O | H |
| propargyl | chlorodifluoromethyl | H | cyclo-propyl | O | H |
| 2,2,2-trifluoroethyl | pentafluoroethyl | H | cyclo-propyl | O | H |
| 2,2,2-trifluoroethyl | methoxymethyl | H | cyclo-propyl | O | H |
| 2,2,2-trifluoroethyl | 1-methylmethoxymethyl | H | cyclo-propyl | O | H |
| 2,2,2-trifluoroethyl | 1-methylmethoxyethyl | H | cyclo-propyl | O | H |
| 2,2,2-trifluoroethyl | ethoxymethyl | H | cyclo-propyl | O | H |
| phenyl | vinyl | H | cyclo-propyl | O | H |
| phenyl | allyl | H | cyclo-propyl | O | H |
| phenyl | methallyl | H | cyclo-propyl | O | H |
| phenyl | crotyl | H | cyclo-propyl | O | H |
| phenyl | ethynyl | H | cyclo-propyl | O | H |
| 2-F-phenyl | propargyl | H | cyclo-propyl | O | H |
| 2-F-phenyl | phenylethinyl | H | cyclo-propyl | O | H |
| 2-F-phenyl | methoxy | H | cyclo-propyl | O | H |
| 2-F-phenyl | ethoxy | H | cyclo-propyl | O | H |
| 2-F-phenyl | iso-propoxy | H | cyclo-propyl | O | H |
| 4-F-phenyl | trifluoromethoxy | H | cyclo-propyl | O | H |
| 4-F-phenyl | methylthio | H | cyclo-propyl | O | H |
| 4-F-phenyl | trifluoromethylthio | H | cyclo-propyl | O | H |
| 4-F-phenyl | phenyl | H | cyclo-propyl | O | H |
| 4-F-phenyl | 4-F-phenyl | H | cyclo-propyl | O | H |
| 2,4,6-(Cl,CF₃Cl)-phenyl | 2-F-phenyl | H | cyclo-propyl | O | H |
| 2,4,6-(Cl,CF₃Cl)-phenyl | 2,4-(Cl,Cl)-phenyl | H | cyclo-propyl | O | H |
| 2,4,6-(Cl,CF₃Cl)-phenyl | 4-CH₃-phenyl | H | cyclo-propyl | O | H |
| 2,4,6-(Cl,CF₃Cl)-phenyl | 4-t-butylphenyl | H | cyclo-propyl | O | H |
| 2,4,6-(Cl,CF₃Cl)-phenyl | 2,4-dimethylphenyl | H | cyclo-propyl | O | H |
| 2,4,6-(Cl,CF₃Cl)-phenyl | 2,4,6-trimethylphenyl | H | cyclo-propyl | O | H |
| 2,4,6-(Cl,CF₃Cl)-phenyl | 2-Cl-phenyl | H | cyclo-propyl | O | H |
| 4-CF₃-phenyl | 3-Cl-phenyl | H | cyclo-propyl | O | H |
| 4-CF₃-phenyl | 4-Cl-phenyl | H | cyclo-propyl | O | H |
| 4-CF₃-phenyl | 4-CN-phenyl | H | cyclo-propyl | O | H |
| 4-CF₃-phenyl | nitro | H | cyclo-propyl | O | H |
| 4-CF₃-phenyl | COOH | H | cyclo-propyl | O | H |
| 4-CF₃-phenyl | 2-CF₃-phenyl | H | cyclo-propyl | O | H |
| 4-CF₃-phenyl | 3-CF₃-phenyl | H | cyclo-propyl | O | H |
| 4-CF₃-phenyl | 4-CF₃-phenyl | H | cyclo-propyl | O | H |
| 4-CF₃-phenyl | 2-OCH₃-phenyl | H | cyclo-propyl | O | H |
| 4-CN-phenyl | 3-OCH₃-phenyl | H | cyclo-propyl | O | H |
| 4-CN-phenyl | 4-OCH₃-phenyl | H | cyclo-propyl | O | H |
| 4-SCF₃-phenyl | S-tert.-butyl | H | cyclo-propyl | O | H |
| 4-SCF₃-phenyl | phenylthio | H | cyclo-propyl | O | H |
| 4-SCF₃-phenyl | 4-F-phenylthio | H | cyclo-propyl | O | H |
| 4-SCF₃-phenyl | S-iso-propyl | H | cyclo-propyl | O | H |
| 4-SCF₃-phenyl | 3-pyridyl | H | cyclo-propyl | O | H |
| 2-pyridyl | 3-thienyl | H | cyclo-propyl | O | H |
| 2-pyridyl | 2-pyridyl | H | cyclo-propyl | O | H |
| 2-pyridyl | 2-thienyl | H | cyclo-propyl | O | H |

TABLE-continued

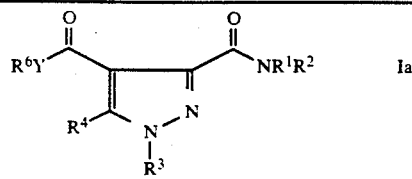

| R³ | R⁴ | R¹ | R² | Y | R⁶ |
|---|---|---|---|---|---|
| 2-pyridyl | cinnamyl | H | cyclo-propyl | O | H |
| 2-pyridyl | 3-(4-F-phenyl)-propenyl | H | cyclo-propyl | O | H |
| 2-pyridyl | 2,4-(NO₂,NO₂)-phenyl | H | cyclo-propyl | O | H |
| H | Cl | H | tert.-butyl | O | —N=C(CH₃)₂ |
| H | Br | H | tert.-butyl | O | —N=C(CH₃)₂ |
| H | methyl | H | tert.-butyl | O | —N=C(CH₃)₂ |
| H | ethyl | H | tert.-butyl | O | —N=C(CH₃)₂ |
| methyl | n-propyl | H | tert.-butyl | O | —N=C(CH₃)₂ |
| methyl | iso-propyl | H | tert.-butyl | O | —N=C(CH₃)₂ |
| methyl | n-butyl | H | tert.-butyl | O | —N=C(CH₃)₂ |
| methyl | iso-butyl | H | tert.-butyl | O | —N=C(CH₃)₂ |
| methyl | sec.-butyl | H | tert.-butyl | O | —N=C(CH₃)₂ |
| allyl | tert.-butyl | H | tert.-butyl | O | —N=C(CH₃)₂ |
| allyl | cyclo-propyl | H | tert.-butyl | O | —N=C(CH₃)₂ |
| allyl | cyclo-butyl | H | tert.-butyl | O | —N=C(CH₃)₂ |
| allyl | cyclo-pentyl | H | tert.-butyl | O | —N=C(CH₃)₂ |
| allyl | cyclo-hexyl | H | tert.-butyl | O | —N=C(CH₃)₂ |
| propargyl | cyclo-heptyl | H | tert.-butyl | O | —N=C(CH₃)₂ |
| propargyl | cyclo-octyl | H | tert.-butyl | O | —N=C(CH₃)₂ |
| propargyl | 1-methylcyclopropyl | H | tert.-butyl | O | —N=C(CH₃)₂ |
| propargyl | trifluoromethyl | H | tert.-butyl | O | —N=C(CH₃)₂ |
| propargyl | chlorodifluoromethyl | H | tert.-butyl | O | —N=C(CH₃)₂ |
| 2,2,2-trifluoroethyl | pentafluoroethyl | H | tert.-butyl | O | —N=C(CH₃)₂ |
| 2,2,2-trifluoroethyl | methoxymethyl | H | tert.-butyl | O | —N=C(CH₃)₂ |
| 2,2,2-trifluoroethyl | 1-methylmethoxymethyl | H | tert.-butyl | O | —N=C(CH₃)₂ |
| 2,2,2-trifluoroethyl | 1-methylmethoxyethyl | H | tert.-butyl | O | —N=C(CH₃)₂ |
| 2,2,2-trifluoroethyl | ethoxymethyl | H | tert.-butyl | O | —N=C(CH₃)₂ |
| phenyl | vinyl | H | tert.-butyl | O | —N=C(CH₃)₂ |
| phenyl | allyl | H | tert.-butyl | O | —N=C(CH₃)₂ |
| phenyl | methallyl | H | tert.-butyl | O | —N=C(CH₃)₂ |
| phenyl | crotyl | H | tert.-butyl | O | —N=C(CH₃)₂ |
| phenyl | ethynyl | H | tert.-butyl | O | —N=C(CH₃)₂ |
| 2-F-phenyl | propargyl | H | tert.-butyl | O | —N=C(CH₃)₂ |
| 2-F-phenyl | phenylethinyl | H | tert.-butyl | O | —N=C(CH₃)₂ |
| 2-F-phenyl | methoxy | H | tert.-butyl | O | —N=C(CH₃)₂ |
| 2-F-phenyl | ethoxy | H | tert.-butyl | O | —N=C(CH₃)₂ |
| 2-F-phenyl | iso-propoxy | H | tert.-butyl | O | —N=C(CH₃)₂ |
| 4-F-phenyl | trifluoromethoxy | H | tert.-butyl | O | —N=C(CH₃)₂ |
| 4-F-phenyl | methylthio | H | tert.-butyl | O | —N=C(CH₃)₂ |
| 4-F-phenyl | trifluoromethylthio | H | tert.-butyl | O | —N=C(CH₃)₂ |
| 4-F-phenyl | phenyl | H | tert.-butyl | O | —N=C(CH₃)₂ |
| 4-F-phenyl | 4-F-phenyl | H | tert.-butyl | O | —N=C(CH₃)₂ |
| 2,4,6-(Cl,CF₃Cl)-phenyl | 2-F-phenyl | H | tert.-butyl | O | —N=C(CH₃)₂ |
| 2,4,6-(Cl,CF₃Cl)-phenyl | 2,4-(Cl,Cl)-phenyl | H | tert.-butyl | O | —N=C(CH₃)₂ |
| 2,4,6-(Cl,CF₃Cl)-phenyl | 4-CH₃-phenyl | H | tert.-butyl | O | —N=C(CH₃)₂ |
| 2,4,6-(Cl,CF₃Cl)-phenyl | 4-t-butylphenyl | H | tert.-butyl | O | —N=C(CH₃)₂ |
| 2,4,6-(Cl,CF₃Cl)-phenyl | 2,4-dimethylphenyl | H | tert.-butyl | O | —N=C(CH₃)₂ |
| 2,4,6-(Cl,CF₃Cl)-phenyl | 2,4,6-trimethylphenyl | H | tert.-butyl | O | —N=C(CH₃)₂ |
| 2,4,6-(Cl,CF₃Cl)-phenyl | 2-Cl-phenyl | H | tert.-butyl | O | —N=C(CH₃)₂ |
| 4-CF₃-phenyl | 3-Cl-phenyl | H | tert.-butyl | O | —N=C(CH₃)₂ |
| 4-CF₃-phenyl | 4-Cl-phenyl | H | tert.-butyl | O | —N=C(CH₃)₂ |
| 4-CF₃-phenyl | 4-CN-phenyl | H | tert.-butyl | O | —N=C(CH₃)₂ |
| 4-CF₃-phenyl | nitro | H | tert.-butyl | O | —N=C(CH₃)₂ |
| 4-CF₃-phenyl | COOH | H | tert.-butyl | O | —N=C(CH₃)₂ |
| 4-CF₃-phenyl | 2-CF₃-phenyl | H | tert.-butyl | O | —N=C(CH₃)₂ |
| 4-CN-phenyl | 3-CF₃-phenyl | H | tert.-butyl | O | —N=C(CH₃)₂ |
| 4-CN-phenyl | 4-CF₃-phenyl | H | tert.-butyl | O | —N=C(CH₃)₂ |
| 4-CN-phenyl | 2-OCH₃-phenyl | H | tert.-butyl | O | —N=C(CH₃)₂ |
| 4-CN-phenyl | 3-OCH₃-phenyl | H | tert.-butyl | O | —N=C(CH₃)₂ |
| 4-CN-phenyl | 4-OCH₃-phenyl | H | tert.-butyl | O | —N=C(CH₃)₂ |
| 4-SCF₃-phenyl | s-tert.-butyl | H | tert.-butyl | O | —N=C(CH₃)₂ |
| 4-SCF₃-phenyl | phenylthio | H | tert.-butyl | O | —N=C(CH₃)₂ |
| 4-SCF₃-phenyl | 4-F-phenylthio | H | tert.-butyl | O | —N=C(CH₃)₂ |
| 4-SCF₃-phenyl | S-iso-propyl | H | tert.-butyl | O | —N=C(CH₃)₂ |
| 4-SCF₃-phenyl | 3-pyridyl | H | tert.-butyl | O | —N=C(CH₃)₂ |
| 2-pyridyl | 3-thienyl | H | tert.-butyl | O | —N=C(CH₃)₂ |
| 2-pyridyl | 2-pyridyl | H | tert.-butyl | O | —N=C(CH₃)₂ |
| 2-pyridyl | 2-thienyl | H | tert.-butyl | O | —N=C(CH₃)₂ |
| 2-pyridyl | cinnamyl | H | tert.-butyl | O | —N=C(CH₃)₂ |
| 2-pyridyl | 3-(4-F-phenyl)-propenyl | H | tert.-butyl | O | —N=C(CH₃)₂ |
| 2-pyridyl | 2,4-(NO₂, NO₂)-phenyl | H | tert.-butyl | O | —N=C(CH₃)₂ |
| H | Cl | H | cyclo-propyl | O | —N=C(CH₃)₂ |

TABLE-continued

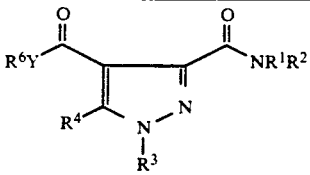

| R³ | R⁴ | R¹ | R² | Y | R⁶ |
|---|---|---|---|---|---|
| H | Br | H | cyclo-propyl | O | $-N=C(CH_3)_2$ |
| H | methyl | H | cyclo-propyl | O | $-N=C(CH_3)_2$ |
| H | ethyl | H | cyclo-propyl | O | $-N=C(CH_3)_2$ |
| methyl | n-propyl | H | cyclo-propyl | O | $-N=C(CH_3)_2$ |
| methyl | iso-propyl | H | cyclo-propyl | O | $-N=C(CH_3)_2$ |
| methyl | n-butyl | H | cyclo-propyl | O | $-N=C(CH_3)_2$ |
| methyl | iso-butyl | H | cyclo-propyl | O | $-N=C(CH_3)_2$ |
| methyl | sec.-butyl | H | cyclo-propyl | O | $-N=C(CH_3)_2$ |
| allyl | tert.-butyl | H | cyclo-propyl | O | $-N=C(CH_3)_2$ |
| allyl | cyclo-propyl | H | cyclo-propyl | O | $-N=C(CH_3)_2$ |
| allyl | cyclo-butyl | H | cyclo-propyl | O | $-N=C(CH_3)_2$ |
| allyl | cyclo-pentyl | H | cyclo-propyl | O | $-N=C(CH_3)_2$ |
| allyl | cyclo-hexyl | H | cyclo-propyl | O | $-N=C(CH_3)_2$ |
| propargyl | cyclo-heptyl | H | cyclo-propyl | O | $-N=C(CH_3)_2$ |
| propargyl | cyclo-octyl | H | cyclo-propyl | O | $-N=C(CH_3)_2$ |
| propargyl | 1-methylcyclopropyl | H | cyclo-propyl | O | $-N=C(CH_3)_2$ |
| propargyl | trifluoromethyl | H | cyclo-propyl | O | $-N=C(CH_3)_2$ |
| propargyl | chlorodifluoromethyl | H | cyclo-propyl | O | $-N=C(CH_3)_2$ |
| 2,2,2-trifluoroethyl | pentafluoroethyl | H | cyclo-propyl | O | $-N=C(CH_3)_2$ |
| 2,2,2-trifluoroethyl | methoxymethyl | H | cyclo-propyl | O | $-N=C(CH_3)_2$ |
| 2,2,2-trifluoroethyl | 1-methylmethoxymethyl | H | cyclo-propyl | O | $-N=C(CH_3)_2$ |
| 2,2,2-trifluoroethyl | 1-methylmethoxyethyl | H | cyclo-propyl | O | $-N=C(CH_3)_2$ |
| 2,2,2-trifluoroethyl | ethoxymethyl | H | cyclo-propyl | O | $-N=C(CH_3)_2$ |
| phenyl | vinyl | H | cyclo-propyl | O | $-N=C(CH_3)_2$ |
| phenyl | allyl | H | cyclo-propyl | O | $-N=C(CH_3)_2$ |
| phenyl | methallyl | H | cyclo-propyl | O | $-N=C(CH_3)_2$ |
| phenyl | crotyl | H | cyclo-propyl | O | $-N=C(CH_3)_2$ |
| phenyl | ethynyl | H | cyclo-propyl | O | $-N=C(CH_3)_2$ |
| 2-F-phenyl | propargyl | H | cyclo-propyl | O | $-N=C(CH_3)_2$ |
| 2-F-phenyl | phenylethinyl | H | cyclo-propyl | O | $-N=C(CH_3)_2$ |
| 2-F-phenyl | methoxy | H | cyclo-propyl | O | $-N=C(CH_3)_2$ |
| 2-F-phenyl | ethoxy | H | cyclo-propyl | O | $-N=C(CH_3)_2$ |
| 2-F-phenyl | iso-propoxy | H | cyclo-propyl | O | $-N=C(CH_3)_2$ |
| 4-F-phenyl | trifluoromethoxy | H | cyclo-propyl | O | $-N=C(CH_3)_2$ |
| 4-F-phenyl | methylthio | H | cyclo-propyl | O | $-N=C(CH_3)_2$ |
| 4-F-phenyl | trifluoromethylthio | H | cyclo-propyl | O | $-N=C(CH_3)_2$ |
| 4-F-phenyl | phenyl | H | cyclo-propyl | O | $-N=C(CH_3)_2$ |
| 4-F-phenyl | 4-F-phenyl | H | cyclo-propyl | O | $-N=C(CH_3)_2$ |
| 2,4,6-(Cl,CF₃Cl)-phenyl | 2-F-phenyl | H | cyclo-propyl | O | $-N=C(CH_3)_2$ |
| 2,4,6-(Cl,CF₃Cl)-phenyl | 2,4-(Cl,Cl)-phenyl | H | cyclo-propyl | O | $-N=C(CH_3)_2$ |
| 2,4,6-(Cl,CF₃Cl)-phenyl | 4-CH₃-phenyl | H | cyclo-propyl | O | $-N=C(CH_3)_2$ |
| 2,4,6-(Cl,CF₃Cl)-phenyl | 4-t-butylphenyl | H | cyclo-propyl | O | $-N=C(CH_3)_2$ |
| 2,4,6-(Cl,CF₃Cl)-phenyl | 2,4-dimethylphenyl | H | cyclo-propyl | O | $-N=C(CH_3)_2$ |
| 2,4,6-(Cl,CF₃Cl)-phenyl | 2,4,6-trimethylphenyl | H | cyclo-propyl | O | $-N=C(CH_3)_2$ |
| 2,4,6-(Cl,CF₃Cl)-phenyl | 2-Cl-phenyl | H | cyclo-propyl | O | $-N=C(CH_3)_2$ |
| 4-CF₃-phenyl | 3-Cl-phenyl | H | cyclo-propyl | O | $-N=C(CH_3)_2$ |
| 4-CF₃-phenyl | 4-Cl-phenyl | H | cyclo-propyl | O | $-N=C(CH_3)_2$ |
| 4-CF₃-phenyl | 4-CN-phenyl | H | cyclo-propyl | O | $-N=C(CH_3)_2$ |
| 4-CF₃-phenyl | nitro | H | cyclo-propyl | O | $-N=C(CH_3)_2$ |
| 4-CF₃-phenyl | COOH | H | cyclo-propyl | O | $-N=C(CH_3)_2$ |
| 4-CF₃-phenyl | 2-CF₃-phenyl | H | cyclo-propyl | O | $-N=C(CH_3)_2$ |
| 4-CN-phenyl | 3-CF₃-phenyl | H | cyclo-propyl | O | $-N=C(CH_3)_2$ |
| 4-CN-phenyl | 4-CF₃-phenyl | H | cyclo-propyl | O | $-N=C(CH_3)_2$ |
| 4-CN-phenyl | 2-OCH₃-phenyl | H | cyclo-propyl | O | $-N=C(CH_3)_2$ |
| 4-CN-phenyl | 3-OCH₃-phenyl | H | cyclo-propyl | O | $-N=C(CH_3)_2$ |
| 4-CN-phenyl | 4-OCH₃-phenyl | H | cyclo-propyl | O | $-N=C(CH_3)_2$ |
| 4-SCF₃-phenyl | s-tert.-butyl | H | cyclo-propyl | O | $-N=C(CH_3)_2$ |
| 4-SCF₃-phenyl | phenylthio | H | cyclo-propyl | O | $-N=C(CH_3)_2$ |
| 4-SCF₃-phenyl | 4-F-phenylthio | H | cyclo-propyl | O | $-N=C(CH_3)_2$ |
| 4-SCF₃-phenyl | S-iso-propyl | H | cyclo-propyl | O | $-N=C(CH_3)_2$ |
| 4-SCF₃-phenyl | 3-pyridyl | H | cyclo-propyl | O | $-N=C(CH_3)_2$ |
| 2-pyridyl | 3-thienyl | H | cyclo-propyl | O | $-N=C(CH_3)_2$ |
| 2-pyridyl | 2-pyridyl | H | cyclo-propyl | O | $-N=C(CH_3)_2$ |
| 2-pyridyl | 2-thienyl | H | cyclo-propyl | O - | $-N=C(CH_3)_2$ |
| 2-pyridyl | cinnamyl | H | cyclo-propyl | O | $-N=C(CH_3)_2$ |
| 2-pyridyl | 3-(4-F-phenyl)-propenyl | H | cyclo-propyl | O | $-N=C(CH_3)_2$ |
| 2-pyridyl | 2,4-(NO₂.NO₂)-phenyl | H | cyclo-propyl | O | $-N=C(CH_3)_2$ |
| H | H | H | methyl | O | H |
| H | H | H | ethyl | O | H |
| H | H | H | n-propyl | O | H |
| H | H | H | iso-propyl | O | H |
| H | H | H | n-butyl | O | H |

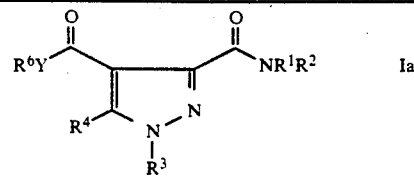

Ia

| R³ | R⁴ | R¹ | R² | Y | R⁶ |
|---|---|---|---|---|---|
| methyl | H | H | iso-butyl | O | H |
| methyl | H | H | sec.-butyl | O | H |
| methyl | H | H | n-pentyl | O | H |
| methyl | H | H | 2-pentyl | O | H |
| methyl | H | H | 3-pentyl | O | H |
| allyl | H | H | n-hexyl | O | H |
| allyl | H | H | 2-hexyl | O | H |
| allyl | H | H | 3-hexyl | O | H |
| allyl | H | H | 2-methyl-2-pentyl | O | H |
| allyl | H | H | cyclo-propylmethyl | O | H |
| propargyl | H | H | cyclo-butyl | O | H |
| propargyl | H | H | cyclo-pentyl | O | H |
| propargyl | H | H | cyclo-hexyl | O | H |
| propargyl | H | H | 1-methylcyclohexyl | O | H |
| propargyl | H | H | 3-trifluoromethylcyclohexyl | O | H |
| 2,2,2-trifluoroethyl | H | H | allyl | O | H |
| 2,2,2-trifluoroethyl | H | H | 1-buten-3-yl | O | H |
| 2,2,2-trifluoroethyl | H | H | crotyl | O | H |
| 2,2,2-trifluoroethyl | H | H | propargyl | O | H |
| 2,2,2-trifluoroethyl | H | H | 1-butyn-3-yl | O | H |
| phenyl | H | H | 3-methyl-1-butyn-3-yl | O | H |
| phenyl | H | H | 2-pentyn-4-yl | O | H |
| phenyl | H | H | benzyl | O | H |
| phenyl | H | H | 2-phenylethyl | O | H |
| phenyl | H | H | 2-methylthioethyl | O | H |
| 2-F-phenyl | H | H | 2-chloroethyl | O | H |
| 2-F-phenyl | H | H | 2-methoxyethyl | O | H |
| 2-F-phenyl | H | H | 2-(N,N-dimethylamino)ethyl | O | H |
| 2-F-phenyl | H | H | phenyl | O | H |
| 2-F-phenyl | H | H | 2-$CH_3$-phenyl | O | H |
| 4-F-phenyl | H | H | 4-$CH_3$-phenyl | O | H |
| 4-F-phenyl | H | H | 2,4-($CH_3$,$CH_3$)-phenyl | O | H |
| 4-F-phenyl | H | H | 2,3,5-($CH_3$,$CH_3$,$CH_3$)-phenyl | O | H |
| 4-F-phenyl | H | H | 3-$CF_3$-phenyl | O | H |
| 4-F-phenyl | H | H | 3-F-phenyl | O | H |
| 2,4,6-(Cl,$CF_3$,Cl)-phenyl | H | H | 2-Cl-phenyl | O | H |
| 2,4,6-(Cl,$CF_3$,Cl)-phenyl | H | H | 4-Cl-phenyl | O | H |
| 2,4,6-(Cl,$CF_3$,Cl)-phenyl | H | H | 2,4-(F,F)-phenyl | O | H |
| 2,4,6-(Cl,$CF_3$,Cl)-phenyl | H | H | 2,3,5-(Cl,Cl,Cl)-phenyl | O | H |
| 2,4,6-(Cl,$CF_3$,Cl)-phenyl | H | H | 2-CN-phenyl | O | H |
| 2,4,6-(Cl,$CF_3$,Cl)-phenyl | H | H | 2-$OCH_3$-phenyl | O | H |
| 2,4,6-(Cl,$CF_3$,Cl)-phenyl | H | H | 2,3-($OCH_3$,$OCH_3$)-phenyl | O | H |
| 4-$CF_3$-phenyl | H | H | 3,4,5-($OCH_3$,$OCH_3$,$OCH_3$)-phenyl | O | H |
| 4-$CF_3$-phenyl | H | H | 3-$OCF_3$-phenyl | O | H |
| 4-$CF_3$-phenyl | H | H | 3-$OCF_2OHF_2$-phenyl | O | H |
| 4-$CF_3$-phenyl | H | H | 4-$OCF_2CHF_2$-phenyl | O | H |
| 4-$CF_3$-phenyl | H | H | 2-$SCH_3$-phenyl | O | H |
| 4-$CF_3$-phenyl | H | H | 2,4-($SCH_3$,$SCH_3$)-phenyl | O | H |
| 4-CN-phenyl | H | H | 2-$SCF_3$-phenyl | O | H |
| 4-CN-phenyl | H | H | 4-$NO_2$-phenyl | O | H |
| 4-CN-phenyl | H | H | 2,4-($NO_2$,$NO_2$)-phenyl | O | H |
| 4-CN-phenyl | H | H | 2-CHO-phenyl | O | H |
| 4-CN-phenyl | H | H | 3-$COCH_3$-phenyl | O | H |
| 4-$SCF_3$-phenyl | H | H | 3-$COCF_3$-phenyl | O | H |
| 4-$SCF_3$-phenyl | H | H | 1-naphthyl | O | H |
| 4-$SCF_3$-phenyl | H | H | 2-naphthyl | O | H |
| 4-$SCF_3$-phenyl | H | H | piperidino | O | H |
| 4-$SCF_3$-phenyl | H | H | 3-tetrahydrofuranyl | O | H |
| 2-pyridyl | H | H | 4-tetrahydropyranyl | O | H |
| 2-pyridyl | H | H | 2-thiazolyl | O | H |
| 2-pyridyl | H | H | 5-$CH_3$-2-thiazolyl | O | H |
| 2-pyridyl | H | H | 4-$CH_3$-5-COOH-2-thiazolyl | O | H |
| 2-pyridyl | H | H | n-propyl | O | H |
| 2-pyridyl | H | H | iso-propyl | O | H |
| H | H | H | methyl | O | $-N=C(CH_3)_2$ |
| H | H | H | ethyl | O | $-N=C(CH_3)_2$ |
| H | H | H | n-propyl | O | $-N=C(CH_3)_2$ |
| H | H | H | iso-propyl | O | $-N=C(CH_3)_2$ |
| H | H | H | n-butyl | O | $-N=C(CH_3)_2$ |
| methyl | H | H | iso-butyl | O | $-N=C(CH_3)_2$ |
| methyl | H | H | sec.-butyl | O | $-N=C(CH_3)_2$ |
| methyl | H | H | n-pentyl | O | $-N=C(CH_3)_2$ |

TABLE-continued

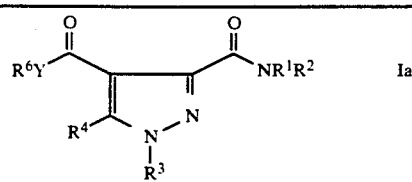

| R³ | R⁴ | R¹ | R² | Y | R⁶ |
|---|---|---|---|---|---|
| methyl | H | H | 2-pentyl | O | —N=C(CH₃)₂ |
| methyl | H | H | 3-pentyl | O | —N=C(CH₃)₂ |
| allyl | H | H | n-hexyl | O | —N=C(CH₃)₂ |
| allyl | H | H | 2-hexyl | O | —N=C(CH₃)₂ |
| allyl | H | H | 3-hexyl | O | —N=C(CH₃)₂ |
| allyl | H | H | 2-methyl-2-pentyl | O | —N=C(CH₃)₂ |
| allyl | H | H | cyclo-propylmethyl | O | —N=C(CH₃)₂ |
| propargyl | H | H | cyclo-butyl | O | —N=C(CH₃)₂ |
| propargyl | H | H | cyclo-pentyl | O | —N=C(CH₃)₂ |
| propargyl | H | H | cyclo-hexyl | O | —N=C(CH₃)₂ |
| propargyl | H | H | 1-methylcyclohexyl | O | —N=C(CH₃)₂ |
| propargyl | H | H | 3-trifluoromethylcyclohexyl | O | —N=C(CH₃)₂ |
| 2,2,2-trifluoroethyl | H | H | allyl | O | —N=C(CH₃)₂ |
| 2,2,2-trifluoroethyl | H | H | 1-buten-3-yl | O | —N=C(CH₃)₂ |
| 2,2,2-trifluoroethyl | H | H | crotyl | O | —N=C(CH₃)₂ |
| 2,2,2-trifluoroethyl | H | H | propargyl | O | —N=C(CH₃)₂ |
| 2,2,2-trifluoroethyl | H | H | 1-butyn-3-yl | O | —N=C(CH₃)₂ |
| phenyl | H | H | 3-methyl-1-butyn-3-yl | O | —N=C(CH₃)₂ |
| phenyl | H | H | 2-pentyn-4-yl | O | —N=C(CH₃)₂ |
| phenyl | H | H | benzyl | O | —N=C(CH₃)₂ |
| phenyl | H | H | 2-phenylethyl | O | —N=C(CH₃)₂ |
| phenyl | H | H | 2-methylthioethyl | O | —N=C(CH₃)₂ |
| 2-F-phenyl | H | H | 2-chloroethyl | O | —N=C(CH₃)₂ |
| 2-F-phenyl | H | H | 2-methoxyethyl | O | —N=C(CH₃)₂ |
| 2-F-phenyl | H | H | 2-(N,N-dimethylamino)ethyl | O | —N=C(CH₃)₂ |
| 2-F-phenyl | H | H | phenyl | O | —N=C(CH₃)₂ |
| 2-F-phenyl | H | H | 2-CH₃-phenyl | O | —N=C(CH₃)₂ |
| 4-F-phenyl | H | H | 4-CH₃-phenyl | O | —N=C(CH₃)₂ |
| 4-F-phenyl | H | H | 2,4-(CH₃,CH₃)-phenyl | O | —N=C(CH₃)₂ |
| 4-F-phenyl | H | H | 2,3,5-(CH₃,CH₃,CH₃)-phenyl | O | —N=C(CH₃)₂ |
| 4-F-phenyl | H | H | 3-CF₃-phenyl | O | —N=C(CH₃)₂ |
| 4-F-phenyl | H | H | 3-F-phenyl | O | —N=C(CH₃)₂ |
| 2,4,6-(Cl,CF₃,Cl)-phenyl | H | H | 2-Cl-phenyl | O | —N=C(CH₃)₂ |
| 2,4,6-(Cl,CF₃,Cl)-phenyl | H | H | 4-Cl-phenyl | O | —N=C(CH₃)₂ |
| 2,4,6-(Cl,CF₃,Cl)-phenyl | H | H | 2,4-(F,F)-phenyl | O | —N=C(CH₃)₂ |
| 2,4,6-(Cl,CF₃,Cl)-phenyl | H | H | 2,3,5-(Cl,Cl,Cl)-phenyl | O | —N=C(CH₃)₂ |
| 2,4,6-(Cl,CF₃,Cl)-phenyl | H | H | 2-CN-phenyl | O | —N=C(CH₃)₂ |
| 2,4,6-(Cl,CF₃,Cl)-phenyl | H | H | 2-OCH₃-phenyl | O | —N=C(CH₃)₂ |
| 2,4,6-(Cl,CF₃,Cl)-phenyl | H | H | 2,3-(OCH₃,OCH₃)-phenyl | O | —N=C(CH₃)₂ |
| 4-CF₃-phenyl | H | H | 3,4,5-(OCH₃,OCH₃,OCH₃)-phenyl | O | —N=C(CH₃)₂ |
| 4-CF₃-phenyl | H | H | 3-OCF₃-phenyl | O | —N=C(CH₃)₂ |
| 4-CF₃-phenyl | H | H | 4-OCF₂OHF₂-phenyl | O | —N=C(CH₃)₂ |
| 4-CF₃-phenyl | H | H | 2-SCH₃-phenyl | O | —N=C(CH₃)₂ |
| 4-CF₃-phenyl | H | H | 2,4-(SCH₃,SCH₃)-phenyl | O | —N=C(CH₃)₂ |
| 4-CF₃-phenyl | H | H | 2-SCF₃-phenyl | O | —N=C(CH₃)₂ |
| 4-CN-phenyl | H | H | 4-NO₂-phenyl | O | —N=C(CH₃)₂ |
| 4-CN-phenyl | H | H | 2,4-(NO₂,NO₂)-phenyl | O | —N=C(CH₃)₂ |
| 4-CN-phenyl | H | H | 2-CHO-phenyl | O | —N=C(CH₃)₂ |
| 4-CN-phenyl | H | H | 3-COCF₃-phenyl | O | —N=C(CH₃)₂ |
| 4-SCF₃-phenyl | H | H | 1-naphthyl | O | —N=C(CH₃)₂ |
| 4-SCF₃-phenyl | H | H | 2-naphthyl | O | —N=C(CH₃)₂ |
| 4-SCF₃-phenyl | H | H | piperidino | O | —N=C(CH₃)₂ |
| 4-SCF₃-phenyl | H | H | 3-tetrahydrofuranyl | O | —N=C(CH₃)₂ |
| 4-SCF₃-phenyl | H | H | 4-tetrahydropyranyl | O | —N=C(CH₃)₂ |
| 2-pyridyl | H | H | 2-thiazolyl | O | —N=C(CH₃)₂ |
| 2-pyridyl | H | H | 5-CH₃-2-thiazolyl | O | —N=C(CH₃)₂ |
| 2-pyridyl | H | H | 4-CH₃-5-COOH-2-thiazolyl | O | —N=C(CH₃)₂ |
| 2-pyridyl | H | H | n-propyl | O | —N=C(CH₃)₂ |
| 2-pyridyl | H | H | iso-propyl | O | —N=C(CH₃)₂ |
| 2-pyridyl | H | H | n-butyl | O | —N=C(CH₃)₂ |
| H | H | H | tert.-butyl | O | 4-hydroxy-2-butynyl |
| H | H | H | tert.-butyl | O | N=C(C₂H₅)₂ |
| H | H | H | tert.-butyl | O | N=C(cyclo-C₃H₅)₂ |
| H | H | H | tert.-butyl | O | 2-butanimino |
| H | H | H | tert.-butyl | O | cyclohexanimino |
| methyl | H | H | tert.-butyl | O | cyclooctanimino |
| methyl | H | H | tert.-butyl | O | N=CH—C₆H₅ |
| methyl | H | H | tert.-butyl | O | 2-furyl-methanimino |
| methyl | H | H | tert.-butyl | O | CH₂CH₂N(CH₃)₂ |
| methyl | H | H | tert.-butyl | O | CH₂CH₂N+(CH₃)₃I |
| allyl | H | H | tert.-butyl | O | CH₂CF₃ |
| allyl | H | H | tert.-butyl | O | CH₂CH₂Cl |

TABLE-continued $$\text{Ia}$$

Structure: pyrazole with R$^6$Y-C(O)- at position 4, -C(O)-NR$^1$R$^2$ at position 3, R$^4$ at position 5, and R$^3$ on N1.

| R$^3$ | R$^4$ | R$^1$ | R$^2$ | Y | R$^6$ |
|---|---|---|---|---|---|
| allyl | H | H | tert.-butyl | O | CH$_2$CH$_2$CN |
| allyl | H | H | tert.-butyl | O | CH$_2$CCl$_3$ |
| allyl | H | H | tert.-butyl | O | CH$_2$CH$_2$Si(CH$_3$)$_3$ |
| propargyl | H | H | tert.-butyl | O | CH$_2$CH$_2$O—N=C(CH$_3$)$_2$ |
| propargyl | H | H | tert.-butyl | O | CH$_2$PO(OC$_2$H$_5$)$_2$ |
| propargyl | H | H | tert.-butyl | O | CH(CH$_3$)CH(OCH$_3$)$_2$ |
| propargyl | H | H | tert.-butyl | O | CH$_2$—CON(C$_2$H$_5$)$_2$ |
| propargyl | H | H | tert.-butyl | O | benzyl |
| 2,2,2-trifluoroethyl | H | H | tert.-butyl | O | 2,4-(Cl,Cl)-benzyl |
| 2,2,2-trifluoroethyl | H | H | tert.-butyl | O | 3-pyridyl-methyl |
| 2,2,2-trifluoroethyl | H | H | tert.-butyl | O | 2-thienyl-methyl |
| 2,2,2-trifluoroethyl | H | H | tert.-butyl | O | 2-tetrahydrofuranyl-methyl |
| 2,2,2-trifluoroethyl | H | H | tert.-butyl | O | 2-furanyl-methyl |
| phenyl | H | H | tert.-butyl | O | 2-pyridyl-methyl |
| phenyl | H | H | tert.-butyl | O | phenyl |
| phenyl | H | H | tert.-butyl | O | 4-F-phenyl |
| phenyl | H | H | tert.-butyl | O | 4-trifluoromethylphenyl |
| phenyl | H | H | tert.-butyl | O | 2-NO$_2$-4-F-phenyl |
| 2-F-phenyl | H | H | tert.-butyl | O | 3,5-(CF$_3$,CF$_3$)-phenyl |
| 2-F-phenyl | H | H | tert.-butyl | O | 4-OCH$_3$-phenyl |
| 2-F-phenyl | H | H | tert.-butyl | O | 4-OCF$_3$-phenyl |
| 2-F-phenyl | H | H | tert.-butyl | O | 4-NHCOCH$_3$-phenyl |
| 2-F-phenyl | H | H | tert.-butyl | O | 2-tetrahydropyranyl |
| 4-F-phenyl | H | H | tert.-butyl | O | 2-tetrahydrofuranyl |
| 4-F-phenyl | H | H | tert.-butyl | O | 1-benzotriazolyl |
| 4-F-phenyl | H | H | tert.-butyl | O | methyl |
| 4-F-phenyl | H | H | tert.-butyl | O | ethyl |
| 4-F-phenyl | H | H | tert.-butyl | O | n-propyl |
| 2,4,6-(Cl,CF$_3$,Cl)-phenyl | H | H | tert.-butyl | O | iso-propyl |
| 2,4,6-(Cl,CF$_3$,Cl)-phenyl | H | H | tert.-butyl | O | n-butyl |
| 2,4,6-(Cl,CF$_3$,Cl)-phenyl | H | H | tert.-butyl | O | iso-butyl |
| 2,4,6-(Cl,CF$_3$,Cl)-phenyl | H | H | tert.-butyl | O | sec.-butyl |
| 2,4,6-(Cl,CF$_3$,Cl)-phenyl | H | H | tert.-butyl | O | tert.-butyl |
| 2,4,6-(Cl,CF$_3$,Cl)-phenyl | H | H | tert.-butyl | O | cyclo-hexyl |
| 2,4,6-(Cl,CF$_3$,Cl)-phenyl | H | H | tert.-butyl | O | cyclopropylmethyl |
| 4-CF$_3$-phenyl | H | H | tert.-butyl | O | ethoxymethyl |
| 4-CF$_3$-phenyl | H | H | tert.-butyl | O | 2-methoxy-ethoxy-methyl |
| 4-CF$_3$-phenyl | H | H | tert.-butyl | O | benzyloxymethyl |
| 4-CF$_3$-phenyl | H | H | tert.-butyl | O | (4-bromobenzoyl)-methyl |
| 4-CF$_3$-phenyl | H | H | tert.-butyl | O | (4-methoxybenzoyl)-methyl |
| 4-CF$_3$-phenyl | H | H | tert.-butyl | O | phthalimidomethyl |
| 4-CN-phenyl | H | H | tert.-butyl | O | methylthiomethyl |
| 4-CN-phenyl | H | H | tert.-butyl | O | 2-thiomethyl-ethyl |
| 4-CN-phenyl | H | H | tert.-butyl | O | CH(C$_6$H$_5$)COOCH$_3$ |
| 4-CN-phenyl | H | H | tert.-butyl | O | phthalimido |
| 4-CN-phenyl | H | H | tert.-butyl | O | tetrahydrophthalimido |
| 4-SCF$_3$-phenyl | H | H | tert.-butyl | O | maleinimido |
| 4-SCF$_3$-phenyl | H | H | tert.-butyl | O | succinimido |
| 4-SCF$_3$-phenyl | H | H | tert.-butyl | O | piperidino |
| 4-SCF$_3$-phenyl | H | H | tert.-butyl | O | Li$^+$ |
| 4-SCF$_3$-phenyl | H | H | tert.-butyl | O | Na$^+$ |
| 2-pyridyl | H | H | tert.-butyl | O | K$^+$ |
| 2-pyridyl | H | H | tert.-butyl | O | NH$_4^+$ |
| 2-pyridyl | H | H | tert.-butyl | O | diisopropylammonium |
| 2-pyridyl | H | H | tert.-butyl | O | 2-hydroxyethyl-ammonium |
| 2-pyridyl | H | H | tert.-butyl | O | allyl |
| 2-pyridyl | H | H | tert.-butyl | O | propargyl |
| H | H | H | cyclo-propyl | O | 4-hydroxy-2-butynyl |
| H | H | H | cyclo-propyl | O | N=C(C$_2$H$_5$)$_2$ |
| H | H | H | cyclo-propyl | O | N=C(cyclo-C$_3$H$_5$)$_2$ |
| H | H | H | cyclo-propyl | O | 2-butanimino |
| H | H | H | cyclo-propyl | O | cyclohexanimino |
| methyl | H | H | cyclo-propyl | O | cyclooctanimino |
| methyl | H | H | cyclo-propyl | O | N=CH—C$_6$H$_5$ |
| methyl | H | H | cyclo-propyl | O | 2-furyl-methanimino |
| methyl | H | H | cyclo-propyl | O | CH$_2$CH$_2$N(CH$_3$)$_2$ |
| methyl | H | H | cyclo-propyl | O | CH$_2$CH$_2$N$^+$(CH$_3$)$_3$I$^-$ |
| allyl | H | H | cyclo-propyl | O | CH$_2$CF$_3$ |
| allyl | H | H | cyclo-propyl | O | CH$_2$CH$_2$Cl |
| allyl | H | H | cyclo-propyl | O | CH$_2$CH$_2$CN |
| allyl | H | H | cyclo-propyl | O | CH$_2$CCl$_3$ |
| allyl | H | H | cyclo-propyl | O | CH$_2$CH$_2$Si(CH$_3$)$_3$ |

TABLE-continued

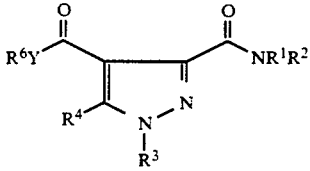

| $R^3$ | $R^4$ | $R^1$ | $R^2$ | Y | $R^6$ |
|---|---|---|---|---|---|
| propargyl | H | H | cyclo-propyl | O | $CH_2CH_2O-N=C(CH_3)_2$ |
| propargyl | H | H | cyclo-propyl | O | $CH_2PO(OC_2H_5)_2$ |
| propargyl | H | H | cyclo-propyl | O | $CH(CH_3)CH(OCH_3)_2$ |
| propargyl | H | H | cyclo-propyl | O | $CH_2-CON(C_2H_5)_2$ |
| propargyl | H | H | cyclo-propyl | O | benzyl |
| 2,2,2-trifluoroethyl | H | H | cyclo-propyl | O | 2,4-(Cl,Cl)-benzyl |
| 2,2,2-trifluoroethyl | H | H | cyclo-propyl | O | 3-pyridyl-methyl |
| 2,2,2-trifluoroethyl | H | H | cyclo-propyl | O | 2-thienyl-methyl |
| 2,2,2-trifluoroethyl | H | H | cyclo-propyl | O | 2-tetrahydrofuranyl-methyl |
| 2,2,2-trifluoroethyl | H | H | cyclo-propyl | O | 2-furanyl-methyl |
| phenyl | H | H | cyclo-propyl | O | 2-pyridyl-methyl |
| phenyl | H | H | cyclo-propyl | O | phenyl |
| phenyl | H | H | cyclo-propyl | O | 4-F-phenyl |
| phenyl | H | H | cyclo-propyl | O | 4-trifluoromethylphenyl |
| phenyl | H | H | cyclo-propyl | O | $2-NO_2-4-F$-phenyl |
| 2-F-phenyl | H | H | cyclo-propyl | O | $3,5-(CF_3,CF_3)$-phenyl |
| 2-F-phenyl | H | H | cyclo-propyl | O | $4-OCH_3$-phenyl |
| 2-F-phenyl | H | H | cyclo-propyl | O | $4-OCF_3$-phenyl |
| 2-F-phenyl | H | H | cyclo-propyl | O | $4-NHCOCH_3$-phenyl |
| 2-F-phenyl | H | H | cyclo-propyl | O | 2-tetrahydropyranyl |
| 4-F-phenyl | H | H | cyclo-propyl | O | 2-tetrahydrofuranyl |
| 4-F-phenyl | H | H | cyclo-propyl | O | 1-benzotriazolyl |
| 4-F-phenyl | H | H | cyclo-propyl | O | methyl |
| 4-F-phenyl | H | H | cyclo-propyl | O | ethyl |
| 2,4,6-$(Cl,CF_3,Cl)$-phenyl | H | H | cyclo-propyl | O | n-propyl |
| 2,4,6-$(Cl,CF_3,Cl)$-phenyl | H | H | cyclo-propyl | O | iso-propyl |
| 2,4,6-$(Cl,CF_3,Cl)$-phenyl | H | H | cyclo-propyl | O | n-butyl |
| 2,4,6-$(Cl,CF_3,Cl)$-phenyl | H | H | cyclo-propyl | O | iso-butyl |
| 2,4,6-$(Cl,CF_3,Cl)$-phenyl | H | H | cyclo-propyl | O | sec.-butyl |
| 2,4,6-$(Cl,CF_3,Cl)$-phenyl | H | H | cyclo-propyl | O | tert.-butyl |
| 2,4,6-$(Cl,CF_3,Cl)$-phenyl | H | H | cyclo-propyl | O | cyclo-hexyl |
| $4-CF_3$-phenyl | H | H | cyclo-propyl | O | cyclopropylmethyl |
| $4-CF_3$-phenyl | H | H | cyclo-propyl | O | ethoxymethyl |
| $4-CF_3$-phenyl | H | H | cyclo-propyl | O | 2-methoxy-ethoxy-methyl |
| $4-CF_3$-phenyl | H | H | cyclo-propyl | O | benzyloxymethyl |
| $4-CF_3$-phenyl | H | H | cyclo-propyl | O | (4-bromobenzoyl)-methyl |
| $4-CF_3$-phenyl | H | H | cyclo-propyl | O | (4-methoxybenzoyl)-methyl |
| 4-CN-phenyl | H | H | cyclo-propyl | O | phthalimidomethyl |
| 4-CN-phenyl | H | H | cyclo-propyl | O | methylthiomethyl |
| 4-CN-phenyl | H | H | cyclo-propyl | O | 2-thiomethyl-ethyl |
| 4-CN-phenyl | H | H | cyclo-propyl | O | $CH(C_6H_5)COOCH_3$ |
| 4-CN-phenyl | H | H | cyclo-propyl | O | phthalimido |
| $4-SCF_3$-phenyl | H | H | cyclo-propyl | O | tetrahydrophthalimido |
| $4-SCF_3$-phenyl | H | H | cyclo-propyl | O | maleinimido |
| $4-SCF_3$-phenyl | H | H | cyclo-propyl | O | succinimido |
| $4-SCF_3$-phenyl | H | H | cyclo-propyl | O | piperidino |
| $4-SCF_3$-phenyl | H | H | cyclo-propyl | O | $Li^+$ |
| $4-SCF_3$-phenyl | H | H | cyclo-propyl | O | $Na^+$ |
| 2-pyridyl | H | H | cyclo-propyl | O | $K^+$ |
| 2-pyridyl | H | H | cyclo-propyl | O | $NH_4^+$ |
| 2-pyridyl | H | H | cyclo-propyl | O | diisopropylammonium |
| 2-pyridyl | H | H | cyclo-propyl | O | 2-hydroxyethyl-ammonium |
| 2-pyridyl | H | H | cyclo-propyl | O | allyl |
| H | H | H | tert.-butyl | S | 2,4-(Cl,Cl)-phenyl |
| H | H | H | tert.-butyl | S | 2-pyridyl |
| H | H | H | tert.-butyl | S | ethyl |
| H | H | H | tert.-butyl | S | iso-propyl |
| H | H | H | tert.-butyl | S | butyl |
| methyl | H | H | tert.-butyl | S | tert.-butyl |
| methyl | H | H | tert.-butyl | S | phenyl |
| methyl | H | H | tert.-butyl | S | 4-F-phenyl |
| methyl | H | H | tert.-butyl | S | $3-CF_3$-phenyl |
| methyl | H | H | tert.-butyl | S | 2,4-(Cl,Cl)-phenyl |
| allyl | H | H | tert.-butyl | S- | 2-pyridyl |
| allyl | H | H | tert.-butyl | S | methyl |
| allyl | H | H | tert.-butyl | S | ethyl |
| allyl | H | H | tert.-butyl | S | iso-propyl |
| allyl | H | H | tert.-butyl | S | butyl |
| propargyl | H | H | tert.-butyl | S | tert.-butyl |
| propargyl | H | H | tert.-butyl | S | phenyl |
| propargyl | H | H | tert.-butyl | S | 4-F-phenyl |
| propargyl | H | H | tert.-butyl | S | $3-CF_3$-phenyl |

TABLE-continued

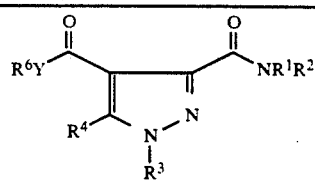

| R³ | R⁴ | R¹ | R² | Y | R⁶ |
|---|---|---|---|---|---|
| propargyl | H | H | tert.-butyl | S | 2,4-(Cl,Cl)-phenyl |
| 2,2,2-trifluoroethyl | H | H | tert.-butyl | S | 2-pyridyl |
| 2,2,2-trifluoroethyl | H | H | tert.-butyl | S | methyl |
| 2,2,2-trifluoroethyl | H | H | tert.-butyl | S | ethyl |
| 2,2,2-trifluoroethyl | H | H | tert.-butyl | S | iso-propyl |
| 2,2,2-trifluoroethyl | H | H | tert.-butyl | S | butyl |
| phenyl | H | H | tert.-butyl | S | tert.-butyl |
| phenyl | H | H | tert.-butyl | S | phenyl |
| phenyl | H | H | tert.-butyl | S | methyl |
| phenyl | H | H | tert.-butyl | S | ethyl |
| phenyl | H | H | tert.-butyl | S | iso-propyl |
| 2-F-phenyl | H | H | tert.-butyl | S | butyl |
| 2-F-phenyl | H | H | tert.-butyl | S | tert.-butyl |
| 2-F-phenyl | H | H | tert.-butyl | S | phenyl |
| 2-F-phenyl | H | H | tert.-butyl | S | 4-F-phenyl |
| 2-F-phenyl | H | H | tert.-butyl | S | 3-CF₃-phenyl |
| 4-F-phenyl | H | H | tert.-butyl | S | 2,4-(Cl,Cl)-phenyl |
| 4-F-phenyl | H | H | tert.-butyl | S | 2-pyridyl |
| 4-F-phenyl | H | H | tert.-butyl | S | methyl |
| 4-F-phenyl | H | H | tert.-butyl | S | ethyl |
| 4-F-phenyl | H | H | tert.-butyl | S | iso-propyl |
| 2,4,6-(Cl,CF₃,Cl)-phenyl | H | H | tert.-butyl | S | butyl |
| 2,4,6-(Cl,CF₃,Cl)-phenyl | H | H | tert.-butyl | S | tert.-butyl |
| 2,4,6-(Cl,CF₃,Cl)-phenyl | H | H | tert.-butyl | S | phenyl |
| 2,4,6-(Cl,CF₃,Cl)-phenyl | H | H | tert.-butyl | S | 4-F-phenyl |
| 2,4,6-(Cl,CF₃,Cl)-phenyl | H | H | tert.-butyl | S | 3-CF₃-phenyl |
| 2,4,6-(Cl,CF₃,Cl)-phenyl | H | H | tert.-butyl | S | 2,4-(Cl,Cl)-phenyl |
| 2,4,6-(Cl,CF₃,Cl)-phenyl | H | H | tert.-butyl | S | 2-pyridyl |
| 4-CF₃-phenyl | H | H | tert.-butyl | S | ethyl |
| 4-CF₃-phenyl | H | H | tert.-butyl | S | iso-propyl |
| 4-CF₃-phenyl | H | H | tert.-butyl | S | butyl |
| 4-CF₃-phenyl | H | H | tert.-butyl | S | tert.-butyl |
| 4-CF₃-phenyl | H | H | tert.-butyl | S | phenyl |
| 4-CF₃-phenyl | H | H | tert.-butyl | S | 4-F-phenyl |
| 4-CN-phenyl | H | H | tert.-butyl | S | 3-CF₃-phenyl |
| 4-CN-phenyl | H | H | tert.-butyl | S | 2,4-(Cl,Cl)-phenyl |
| 4-CN-phenyl | H | H | tert.-butyl | S | 2-pyridyl |
| 4-CN-phenyl | H | H | tert.-butyl | S | methyl |
| 4-CN-phenyl | H | H | tert.-butyl | S | ethyl |
| 4-SCF₃-phenyl | H | H | tert.-butyl | S | iso-propyl |
| 4-SCF₃-phenyl | H | H | tert.-butyl | S | butyl |
| 4-SCF₃-phenyl | H | H | tert.-butyl | S | tert.-butyl |
| 4-SCF₃-phenyl | H | H | tert.-butyl | S | phenyl |
| 4-SCF₃-phenyl | H | H | tert.-butyl | S | 4-F-phenyl |
| 2-pyridyl | H | H | tert.-butyl | S | 3-CF₃-phenyl |
| 2-pyridyl | H | H | tert.-butyl | S | 2,4-(Cl,Cl)-phenyl |
| 2-pyridyl | H | H | tert.-butyl | S | 2-pyridyl |
| 2-pyridyl | H | H | tert.-butyl | S | methyl |
| 2-pyridyl | H | H | tert.-butyl | S | ethyl |
| 2-pyridyl | H | H | tert.-butyl | S | iso-propyl |
| H | H | H | cyclo-propyl | S | butyl |
| H | H | H | cyclo-propyl | S | tert.-butyl |
| H | H | H | cyclo-propyl | S | phenyl |
| H | H | H | cyclo-propyl | S | 4-F-phenyl |
| H | H | H | cyclo-propyl | S | 3-CF₃-phenyl |
| methyl | H | H | cyclo-propyl | S | 2,4-(Cl,Cl)-phenyl |
| methyl | H | H | cyclo-propyl | S | 2-pyridyl |
| methyl | H | H | cyclo-propyl | S | methyl |
| methyl | H | H | cyclo-propyl | S | ethyl |
| methyl | H | H | cyclo-propyl | S | iso-propyl |
| allyl | H | H | cyclo-propyl | S | butyl |
| allyl | H | H | cyclo-propyl | S | tert.-butyl |
| allyl | H | H | cyclo-propyl | S | phenyl |
| allyl | H | H | cyclo-propyl | S | methyl |
| allyl | H | H | cyclo-propyl | S | ethyl |
| propargyl | H | H | cyclo-propyl | S | iso-propyl |
| propargyl | H | H | cyclo-propyl | S | butyl |
| propargyl | H | H | cyclo-propyl | S | tert.-butyl |
| propargyl | H | H | cyclo-propyl | S | phenyl |
| propargyl | H | H | cyclo-propyl | S | 4-F-phenyl |
| 2,2,2-trifluoroethyl | H | H | cyclo-propyl | S | 3-CF₃-phenyl |
| 2,2,2-trifluoroethyl | H | H | cyclo-propyl | S | 2,4-(Cl,Cl)-phenyl |

TABLE-continued

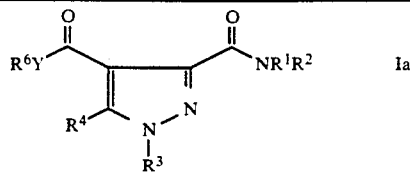

| $R^3$ | $R^4$ | $R^1$ | $R^2$ | Y | $R^6$ |
| --- | --- | --- | --- | --- | --- |
| 2,2,2-trifluoroethyl | H | H | cyclo-propyl | S | 2-pyridyl |
| 2,2,2-trifluoroethyl | H | H | cyclo-propyl | S | methyl |
| 2,2,2-trifluoroethyl | H | H | cyclo-propyl | S | ethyl |
| phenyl | H | H | cyclo-propyl | S | iso-propyl |
| phenyl | H | H | cyclo-propyl | S | butyl |
| phenyl | H | H | cyclo-propyl | S | tert.-butyl |
| phenyl | H | H | cyclo-propyl | S | phenyl |
| phenyl | H | H | cyclo-propyl | S | 4-F-phenyl |
| 2-F-phenyl | H | H | cyclo-propyl | S | 3-CF$_3$-phenyl |
| 2-F-phenyl | H | H | cyclo-propyl | S | 2,4-(Cl,Cl)-phenyl |
| 2-F-phenyl | H | H | cyclo-propyl | S | 2-pyridyl |
| 2-F-phenyl | H | H | cyclo-propyl | S | ethyl |
| 2-F-phenyl | H | H | cyclo-propyl | S | iso-propyl |
| 4-F-phenyl | H | H | cyclo-propyl | S | butyl |
| 4-F-phenyl | H | H | cyclo-propyl | S | tert.-butyl |
| 4-F-phenyl | H | H | cyclo-propyl | S | phenyl |
| 4-F-phenyl | H | H | cyclo-propyl | S | 4-F-phenyl |
| 4-F-phenyl | H | H | cyclo-propyl | S | 3-CF$_3$-phenyl |
| 2,4,6-(Cl,CF$_3$,Cl)-phenyl | H | H | cyclo-propyl | S | 2,4-(Cl,Cl)-phenyl |
| 2,4,6-(Cl,CF$_3$,Cl)-phenyl | H | H | tert.-butyl | S | 2-pyridyl |
| 2,4,6-(Cl,CF$_3$,Cl)-phenyl | H | H | cyclo-propyl | S | ethyl |
| 2,4,6-(Cl,CF$_3$,Cl)-phenyl | H | H | cyclo-propyl | S | iso-propyl |
| 2,4,6-(Cl,CF$_3$,Cl)-phenyl | H | H | cyclo-propyl | S | butyl |
| 2,4,6-(Cl,CF$_3$,Cl)-phenyl | H | H | cyclo-propyl | S | tert.-butyl |
| 2,4,6-(Cl,CF$_3$,Cl)-phenyl | H | H | cyclo-propyl | S | phenyl |
| 4-CF$_3$-phenyl | H | H | cyclo-propyl | S | 4-F-phenyl |
| 4-CF$_3$-phenyl | H | H | cyclo-propyl | S | 3-CF$_3$-phenyl |
| 4-CF$_3$-phenyl | H | H | cyclo-propyl | S | 2,4-(Cl,Cl)-phenyl |
| 4-CF$_3$-phenyl | H | H | cyclo-propyl | S | 2-pyridyl |
| 4-CF$_3$-phenyl | H | H | cyclo-propyl | S | methyl |
| 4-CF$_3$-phenyl | H | H | cyclo-propyl | S | ethyl |
| 4-CN-phenyl | H | H | cyclo-propyl | S | iso-propyl |
| 4-CN-phenyl | H | H | cyclo-propyl | S | butyl |
| 4-CN-phenyl | H | H | cyclo-propyl | S | tert.-butyl |
| 4-CN-phenyl | H | H | cyclo-propyl | S | phenyl |
| 4-CN-phenyl | H | H | cyclo-propyl | S | 4-F-phenyl |
| 4-SCF$_3$-phenyl | H | H | cyclo-propyl | S | 3-CF$_3$-phenyl |
| 4-SCF$_3$-phenyl | H | H | cyclo-propyl | S | 2,4-(Cl,Cl)-phenyl |
| 4-SCF$_3$-phenyl | H | H | cyclo-propyl | S | 2-pyridyl |
| 4-SCF$_3$-phenyl | H | H | cyclo-propyl | S | methyl |
| 4-SCF$_3$-phenyl | H | H | cyclo-propyl | S | ethyl |
| 2-pyridyl | H | H | cyclo-propyl | S | iso-propyl |
| 2-pyridyl | H | H | cyclo-propyl | S | butyl |
| 2-pyridyl | H | H | cyclo-propyl | S | tert.-butyl |
| 2-pyridyl | H | H | cyclo-propyl | S | phenyl |
| 2-pyridyl | H | H | cyclo-propyl | S | methyl |
| 2-pyridyl | H | H | cyclo-propyl | S | ethyl |

Suitable salts of compounds of the formula Ia are agriculturally useful salts, for example alkali metal salts, such as potassium and sodium salts, alkaline earth metal salts, such as calcium, magnesium and barium salts, manganese, copper, zinc or iron salts, e.g., ammonium salts, tetraalkylammonium salts, benzyltrialkylammonium salts, trialkylsulfonium salts and trialkylsulfoxonium salts.

The herbicidal compounds I, or agents containing them, may be applied for instance in the form of directly sprayable solutions, powders, suspensions (including high-percentage aqueous, oily or other suspensions), dispersions, emulsions, oil dispersions, pastes, dusts broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth methal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are used in a purity of 90 to 100, and preferably 95 to 100, % (according to the NMR spectrum).

Compounds I according to the invention may be formulated as follows:

I. 90 parts by weight of compound no. 1.014 is mixed with 10 parts by weight of N-methyl-alpha-pyrrolidone. A mixture is obtained which is suitable for application in the form of very fine drops.

II. 20 parts by weight of compound no. 1.022 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mol of castor oil. By pouring the solution into 100,000 parts by weight of water and uniformly distributing it therein, an aqueous dispersion is obtained containing 0.02% by weight of the active ingredient.

III. 20 parts by weight of compound no. 1.008 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.040 is dissolved in a mixture consisting of 25 parts by weight of cyclohexnanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1.014 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.016 is intimately mixed with 97 parts by weight of particulate kaolin. A dust is obtained containing 3% by weight of the active ingredient.

VII. 30 parts by weight of compound no. 1.022 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1.004 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stably oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

When the active ingredients are used as herbicides, the application rates depend on the objective to be achieved, the time of the year, the plants to be combated with their growth stage, and are from 0.001 to 5, preferably 0.01 to 2, kg of active ingredient per hectare.

To increase the spectrum of action and to achieve synergistic effects, the compounds I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinone, uracils, benzofuran derivatives, cyclohexane-1,3-dione derivatives, quinolinecarboxylic acids, (hetero)-aryloxyphenoxypropionic acids and salts, esters, amides thereof, etc.

It may also be useful to apply the herbicidal compounds Ia, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The directions given in the synthesis examples below were used, after appropriate modification of the starting materials, to obtain further compounds Ia. The compounds thus obtained are given below with their physical data.

MANUFACTURING EXAMPLES

1.
1(H)-4-ethoxycarbonyl-1-methylpyrazole-3-carboxylic acid

A solution of 10.5 g (50 mmol) of diethyl 1(H)-1-methylpyrazole-3,4-dicarboxylate (J. Org. Chem. 31, 2491 (1966)) in 200 ml of ethanol/water (1:1) was cooled to 0° C., and a solution of 1.96 g (0.049 mol) of sodium hydroxide solution in 50 mol of water was dripped in over a 30-minute period. The mixture was allowed to stand for 14 hours at room temperature, the solvent mixture was removed under reduced pressure, the solid residue was taken up in 100 ml of water and acidified with 10% strength hydrochloric acid, and the precipitated solid was removed by suction filtration. There was obtained 7.40 g (74%) of the hemiester of m.p. 182° C. (from water) as a white powder.

2.
1(H)-4-ethoxycarbonyl-1-methylpyrazole-3-carboxylic acid chloride 7.20 g (36 mmol) of 1(H)-4-ethoxycarbonyl-1-methylpyrazole-3-carboxylic acid from Example 1 was introduced in portions into 20 ml of thionyl chloride, and the whole was refluxed for 2 hours. Excess thionyl chloride was then removed under reduced pressure, the residue was taken up in 50 ml of diethyl ether and the whole was stirred for 30 minutes with 2.00 g of activated carbon. After filtration the filtrate was concentrated under reduced pressure. The residue was 7.30 g (94%) of the acid chloride as a white solid having a melting point of 65° C.

3.
1(H)-4-ethoxycarbonyl-1-methylpyrazole-3-carboxylic isopropylamide 4.00 g (68 mmol) of isopropylamine was dissolved at 0° C. in 100 ml of dichloromethane, the solution obtained was cooled to −10° C., and over a period of 30 minutes at this temperature a solution of 7.20 g (33 mmol) of 1(H)-4-ethoxycarbonyl-1-methylpyrazole-3-carboxylic acid chloride from Example 2 in 20 ml of dichloromethane was dripped in. After all had been added, the mixture was allowed to warm up to room temperature, after which it was stirred for 2 hours and then hydrolyzed by adding 100 ml of 10% strength hydrochloric acid. The organic phase was separated off, dried with sodium sulfate and evaporated down. The residue was 7.20 g (91%) of the amide as a white solid having a melting point of 134° C. (from a 1:1 mixture of cyclohexane/ethyl acetate).

4.
1(H)-1-methyl-3-(isopropylaminocarbonyl)-pyrazole-4-carboxylic acid

A mixture of 7.00 g (29 mmol) of 1(H)-4-ethoxycarbonyl-1-methylpyrazole-3-carboxylic isopropylamide from Example 3 and 1.85 g (33 mmol) of potassium hydroxide in 60 ml of a 1:1 mixture of water and methanol was heated at 60° C. for 3 hours. The solvent mixture was then reduced under reduced pressure and the solid residue was taken up in 20 ml of water. The mixture was acidified with concentrated hydrochloric acid and the precipitated product was suction filtered, giving 6.00 g (98%) of the carboxylic acid as a white solid having a melting point of 180° C. (from methanol) (active ingredient no. 1001).

5.
1(H)-3-(2-chlorobenzylaminocarbonyl)-1-methyl-pyrazole-4-carboxylic acid A mixture of 2.55 g (18 mmol) of 2-chlorobenzylamine and 2.00 g (20 mmol) of triethylamine in 50 ml of dichloromethane was cooled to 0° C. and a solution of 4.00 g (18 mmol) of 1(H)-4-ethoxycarbonyl-1-methylpyrazole-3-carboxylic acid chloride from Example 2 in 20 ml of dichloromethane. The mixture was allowed to heat up to room temperature, after which it was stirred for 2 hours and then hydrolyzed by adding 50 ml of 10% strength hydrochloric acid, and the organic phase was separated. The mixture was concentrated in a rotary evaporator, the residue was taken up with 50 ml of a 1:1 mixture of water and methanol, and a solution of 1.12 g (20 mmol) of potassium hydroxide in 20 ml of water was added. The resulting mixture was heated for 2 hours at 65° C. and free from solvent under reduced pressure, and the residue was taken up with 50 ml of water. This mixture was acidified with concentrated hydrochloric acid, and the precipitated product was suction filtered. There was obtained 5.00 g (95%) of the amide of melting point 154° C. (active ingredient no. 1.018).

6.
1(H)-1-methyl-4-(2-propaniminoxycarbonyl)-pyrazole-3-carboxylic acid tert-butylamide Over a period of 30 minutes, a mixture of 4.50 g (20 mmol) of 1(H)-3-tert-butylaminocarbonyl-1-methylpyrazole-4-carboxylic acid, 1.50 g (20 mmol) of acetonoxime and 4.80 g (48 mmol) of triethylamine in 20 ml of dichloromethane was dripped into a suspension of 6.12 g (24 mmol) of 1-methyl-2-chloropyridinium iodide in 20 ml of dichloromethane. After all had been added, the mixture was refluxed for 3 hours, the solvent was removed under reduced pressure and the residue was purified by chromatography on silica gel using as eluant a 5:1 dichloromethane/ethyl acetate mixture. There was thus obtained 4.40 g (80%) of the oxime ester as a white solid having a melting point of 111° C. (active ingredient no. 1.014).

The compounds given in the table below were prepared analogously to the examples above.

TABLE 1

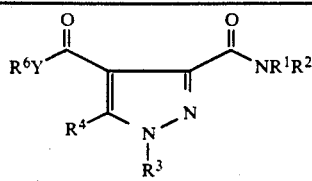 Ia

| Example no. | R³ | R⁴ | R¹ | R² | Y | R⁶ | Melting point [°C.] |
|---|---|---|---|---|---|---|---|
| 1.001 | methyl | H | H | isopropyl | O | H | 180 |
| 1.002 | H | H | H | isopropyl | O | H | 182 |
| 1.003 | methyl | H | H | 4-(Cl)-phenyl | O | H | 251 |
| 1.004 | methyl | H | H | 4-(F)-phenyl | O | H | 248 |
| 1.005 | methyl | H | H | 2-(F)-phenyl | O | H | 196 |
| 1.006 | methyl | H | H | 4-(CF₃)-phenyl | O | H | 225 |
| 1.007 | methyl | H | H | 4-(CF₃)-phenyl | O | ethyl | 220 |
| 1.008 | methyl | H | H | 4-(Cl)-phenyl | O | ethyl | 160 |
| 1.009 | methyl | H | H | 4-(F)-phenyl | O | ethyl | 290 |
| 1.010 | methyl | H | H | 2-(F)-phenyl | O | ethyl | 140 |
| 1.011 | methyl | H | H | tert.-butyl | O | H | 149 |
| 1.012 | methyl | H | H | —O-benzyl | O | H | 98 |
| 1.013 | methyl | H | H | OH | O | H | 219 |
| 1.014 | methyl | H | H | tert.-butyl | O | —N=C(CH₃)₂ | 111 |
| 1.015 | methyl | H | H | (CH₂F)₂—CH— | O | H | 140 |
| 1.016 | methyl | H | H | HC≡C—CH(CH₃)— | O | H | 174 |
| 1.017 | methyl | H | H | cyclopropyl | O | H | 208 |
| 1.018 | methyl | H | H | 2-(Cl)-benzyl | O | H | 154 |
| 1.019 | methyl | H | H | CH(COOC₂H₅)—CH—(CH₃)₂ | O | ethyl | 110 |
| 1.020 | methyl | H | methyl | methyl | O | H | 159 |
| 1.021 | methyl | H | H | C(CH₃)₂—C≡CH | O | H | 188 |
| 1.022 | H | H | H | tert.-butyl | O | H | 200 |
| 1.023 | methyl | H | H | CH(COOH)—CH(CH₃)₂ | O | H | resin |
| 1.024 | H | H | H | 2-(Cl)-benzyl | O | methyl | 172 |
| 1.025 | H | H | H | 2-(Cl)-benzyl | O | H | 298 |
| 1.026 | H | H | H | cyclopropyl | O | H | 212 |
| 1.027 | H | H | H | CH(CH₃)—C≡CH | O | H | 201 |
| 1.028 | H | methyl | H | tert.-butyl | O | H | 276 |
| 1.029 | H | methyl | H | tert.-butyl | O | methyl | 143 |
| 1.030 | phenyl | Br | H | tert.-Butyl | O | H | 192 |
| 1.031 | phenyl | Br | H | cyclo-Propyl | O | H | 227 |
| 1.032 | 4-(CF₃)-phenyl | H | H | cyclo-Propyl | O | H | 211 |
| 1.033 | 4-trifluoromethylphenyl | H | H | tert.-butyl | O | H | 170 |
| 1.034 | 4-fluorophenyl | H | H | tert.-butyl | O | H | 210 |
| 1.035 | 4-fluorophenyl | H | H | cyclopropyl | O | H | 200 |
| 1.036 | 2-(i-propyl)-phenyl | H | H | cyclopropyl | O | H | 68 |
| 1.037 | 2-(i-propyl)-phenyl | H | H | tert.-butyl | O | H | 134 |
| 1.038 | 5,6,7,8-tetrahydro-naphthyl | H | H | tert.-butyl | O | H | 80 |
| 1.039 | 5,6,7,8-tetrahydro-naphthyl | H | H | cyclopropyl | O | H | 88 |
| 1.040 | 4-(t-butyl)-phenyl | H | H | tert.-butyl | O | H | 98 |
| 1.041 | methyl | H | H | CH(CH(CH₃)₂)CO₂CH₂CH₃ | O | H | 110 |
| 1.042 | 4-fluorophenyl | H | H | C(CH₃)(CH(CH₃)₂)—CONH₂ | O | CH₃ | 177 |
| 1.043 | 4-methoxy-phenyl | H | H | tert.-butyl | O | H | 133 |
| 1.044 | 2,4,6-trimethyl-phenyl | H | H | tert.-butyl | O | H | 164 |
| 1.045 | 2-methoxy-phenyl | H | H | tert.-butyl | O | H | 81 |
| 1.046 | 3-trifluoromethoxy-phenyl | H | H | tert.-butyl | O | H | 174 |

TABLE 1-continued

Formula Ia: pyrazole with R⁴ at position 5, N-R³, COYR⁶ at position 4, and CONR¹R² at position 3.

| Example no. | $R^3$ | $R^4$ | $R^1$ | $R^2$ | Y | $R^6$ | Melting point [°C.] |
|---|---|---|---|---|---|---|---|
| 1.047 | 3-trifluoromethylphenyl | H | H | tert.-butyl | O | H | 178 |
| 1.048 | 3-trifluoromethylphenyl | H | H | C(CH$_3$)—CONH$_2$ \| CH(CH$_3$)$_2$ | O | CH$_3$ | 203 |
| 1.049 | 3-trifluoromethylphenyl | H | H | C(CH$_3$)$_2$—CONH$_2$ \| CH(CH$_3$)$_2$ | O | H | 221 |
| 1.050 | 3,5-dichloro-2-methoxy-phenyl | H | H | tert.-butyl | O | H | 90 |
| 1.051 | 2-methylthio-phenyl | H | H | tert.-butyl | O | H | 141 |
| 1.052 | 3-chloro-4-methyl-thio-phenyl | H | H | tert.-butyl | O | H | 221 |
| 1.053 | methyl | H | H | tert.-butyl | O | C$_2$H$_5$ | 145 |
| 1.054 | 4-methylthio-phenyl | H | H | tert.-butyl | O | H | 143 |
| 1.055 | 2,4-dimethyl-phenyl | H | H | tert.-butyl | O | H | 118–120 |
| 1.056 | 2,4-difluorophenyl | H | H | tert.-butyl | O | H | 150–152 |
| 1.057 | 2-chloro-4-methoxy-phenyl | H | H | tert.-butyl | O | H | 198–200 |
| 1.058 | 4-chloro-2-methyl-phenyl | H | H | tert.-butyl | O | H | 98–100 |
| 1.059 | 4-fluoro-2-methyl-phenyl | H | H | tert.-butyl | O | H | 144–146 |
| 1.060 | 4-cyano-phenyl | H | H | tert.-butyl | O | H | 300 |

USE EXAMPLES

The herbicidal action of the pyrazole-3-carboxamides of the formula Ia is demonstrated in greenhouse experiments:

The vessels employed were plastic flowerpots having a volume of 300 cm$^3$ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water. The application rate for postemergence treatment was 1.0 kg/ha.

The pots were set up in the greenhouse, heat-loving species at 20° to 35° C, and species from moderate climates at 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the experiments were *Chenopodium album*, *Sinapis alba* and *Solanum nigrum*.

Active ingredient nos. 1.014 and 1.022, applied postemergence at a rate of 1.0 kg/ha, provided excellent control of unwanted broadleaved plants.

We claim:

1. A pyrazole-3-carboxamide of the formula I

Formula I: pyrazole with R⁵ at position 5, R⁴ at position 4, N-R³, and CONR¹R² at position 3.

where the substituents have the following meanings:
$R^1$ is hydrogen, or C$_1$–C$_6$-alkyl;
$R^2$ is hydrogen or C$_1$–C$_6$ alkyl;
$R^3$ is hydrogen or C$_1$–C$_6$ alkyl;
$R^4$ is hydrogen or C$_1$–C$_6$ alkyl;
$R^5$ is a COYR$^6$ group;
Y is oxygen;
$R^6$ is hydrogen or C$_1$–C$_6$ alkyl.

2. A pyrazole-3-carboxamide of the general formula I as set forth in claim 1, where the substituents have the following meanings:
$R^1$ hydrogen;
$R^2$ C$_1$–C$_4$-alkyl
$R^3$ hydrogen; C$_1$–C$_4$-alkyl;
$R^4$ hydrogen;
$R^5$ a group COYR$^6$;
Y oxygen;
$R^6$ hydrogen.

3. A pyrazole-3-carboxamide of formula I as described in claim 1, wherein $R^1$ and $R^2$ are hydrogen or unsubstituted $C_1$-$C_6$-alkyl.

4. A pyrazole-3-carboxamide of formula I as described in claim 1, wherein $R^1$ and $R^2$ have the meanings recited in claim 1 with the provisos that they are not simultaneously hydrogen and are not simultaneously unsubstituted $C_1$-$C_6$-alkyl.

5. A herbicidal composition containing at least one pyrazole-3-carboxamide of the formula I as set forth in claim 1 and conventional inert additives.

6. A process for combating the growth of unwanted plants, wherein the unwanted plants and/or their habitat are treated with a herbicidally effective amount of a pyrazole-3-carboxamide I as set forth in claim 1.

* * * * *

UNITED STATES PATENT AND TRADEMARK OFFICE
CERTIFICATE OF CORRECTION

PATENT NO. : 5,217,523

DATED : June 8, 1993

INVENTOR(S) : DITRICH et al.

It is certified that error appears in the above-identified patent and that said Letters Patent is hereby corrected as shown below:

On the title page, Item [57]: Abstract, between lines 24 and 25, after formula, insert --oxygen or sulfur;--.

Signed and Sealed this

Twenty-ninth Day of March, 1994

Attest:

BRUCE LEHMAN

Attesting Officer   Commissioner of Patents and Trademarks